United States Patent
Ledis et al.

(10) Patent No.: US 7,083,936 B2
(45) Date of Patent: Aug. 1, 2006

(54) AMINODEXTRAN COMPOSITIONS AND CONJUGATES AND METHOD OF MAKING AND USING THEM

(75) Inventors: Stephen L. Ledis, Pembroke Pines, FL (US); Olavi Siiman, Davie, FL (US); Cynthia G. Healy, Miami, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 537 days.

(21) Appl. No.: 10/633,382

(22) Filed: Aug. 1, 2003

(65) Prior Publication Data

US 2005/0026305 A1  Feb. 3, 2005

(51) Int. Cl.
*G01N 33/567* (2006.01)

(52) U.S. Cl. ............... 435/7.21; 436/518; 436/524; 436/525; 427/2.11; 427/2.13; 427/2.14; 427/127; 427/128; 427/129; 427/7.13; 435/5; 435/7.92; 435/177; 435/178; 435/180; 530/812; 530/813; 530/815; 530/816

(58) Field of Classification Search ............. 436/518, 436/524, 525; 427/2.11, 2.13, 2.14, 127, 427/128, 129, 7.13; 435/5, 7.92, 177, 178, 435/180; 530/813, 815, 816
See application file for complete search history.

(56) References Cited

U.S. PATENT DOCUMENTS

| | | |
|---|---|---|
| 4,542,104 A | 9/1985 | Stryer et al. |
| 5,171,846 A | 12/1992 | Gupta |
| 5,272,257 A | 12/1993 | Gupta |
| 5,424,297 A | 6/1995 | Rubio et al. |
| 5,466,609 A | 11/1995 | Siiman et al. |
| 5,527,713 A | 6/1996 | Bolton et al. |
| 5,543,332 A | 8/1996 | Lihme et al. |
| 5,627,078 A | 5/1997 | Karl et al. |
| 5,658,741 A | 8/1997 | Bolton et al. |
| 5,891,741 A | 4/1999 | Siiman et al. |

(Continued)

FOREIGN PATENT DOCUMENTS

WO  WO 00/07019  2/2000

OTHER PUBLICATIONS

Cairo, C.W., et al., "Control of Multivalent Interactions by Binding Epitope Density", *J. Am. Chem. Soc.*, 124(8), pp. 1615-1619 (2002).

(Continued)

*Primary Examiner*—Long V. Le
*Assistant Examiner*—Pensee T. Do
(74) *Attorney, Agent, or Firm*—Howson and Howson; Mitchell E. Alter

(57) ABSTRACT

A composition containing polydisperse aminodextran polymer molecules is soluble in an aqueous solution at a concentration of 10 mg/ml. The molecules therein have a narrow size distribution characterized by an average molecule mean hydrodynamic diameter of greater than 115 nm, a polydispersity index of between 0.10 and 0.47, an average molecular weight (MW) greater than 3 million daltons, and an amine content of greater than 50 amines per molecule. Similar soluble compositions contain the polymer molecules with an average MW of greater than 7 million daltons. These compositions are useful in forming reagents by conjugation with proteins for labeling cells. Methods of making these compositions and reagents from conventional mixtures of aminodextran polymers involve fractionation on column chromatography.

20 Claims, 14 Drawing Sheets

U.S. PATENT DOCUMENTS

| | | |
|---|---|---|
| 5,945,293 A | 8/1999 | Siiman et al. |
| 5,994,089 A | 11/1999 | Siiman et al. |
| 6,074,884 A | 6/2000 | Siiman et al. |
| 6,207,385 B1 | 3/2001 | Stanley |
| 6,287,568 B1 | 9/2001 | Wang et al. |
| 6,387,622 B1 | 5/2002 | Siiman et al. |

OTHER PUBLICATIONS

T.M. Hansen, "Fluorescent dextran conjugates for use in quantitative assays", *IVD Technol.*, pp. 35-40 (Apr. 2003).

Siiman, et al, "Fluorescent neoglycoproteins: Antibody-Aminodextran-Phycobiliprotein Conjugates", *Bioconjugate Chem.*, 10(6), pp. 1090-1106 (1999).

Comparison of Direct Bottled Product, CD4-ECD, to Two Fractions of Amplified Conjugate, CD4-Dex-ECD, Made with Fractionated Amdex Amplified Conjugate, Streptavidin-Dex-PE, Bound to CD4-Biotin, Standard Process Comparison of Direct Amplified Conjugate, CD8β-Dex-PC5, to Standard Direct Bottled Product

AMINODEXTRAN COMPOSITIONS AND CONJUGATES AND METHOD OF MAKING AND USING THEM

BACKGROUND OF THE INVENTION

Aminodextran (often abbreviated "Amdex") is a high molecular weight polymer comprising a mostly linear chain of glucose residues with chemically introduced pendant amino groups. These amino groups can be activated and conjugated to a variety of proteins. Because of its low nonspecific background binding to cells, its high water solubility, and its ability to vary its amine content by adjustment of reaction conditions, the aminodextran polymer has long been useful as a component of amplified labeled conjugates with proteins, such as streptavidin or monoclonal antibodies. The preferred label in such conjugates is a fluorescent label. Fluorescent proteins, such as phycoerythrin, have also been attached in large numbers to the aminodextran polymer to produce reagents with high specificity and enhanced fluorescent intensity. Numerous such particles have been described as reagents for use in cell labeling for flow cytometry uses. See, for example, the inventor's prior publications including U.S. Pat. Nos. 5,891,741; 5,994,089 and 6,387,622, among others, as well as O. Siiman et al, 1999 *Bioconj. Chem.*, 10(6):1090–1106.

Other uses of aminodextran and aminodextran-protein conjugates are described in, e.g., U.S. Pat. No. 5,424,297 which refers to adenosine dextran conjugates for treating hypertension; U.S. Pat. No. 5,543,332 which refers to other water-soluble conjugates and reagents; and U.S. Pat. No. 6,287,568, which describes immunogenic dextran-protein conjugates for use as vaccines and adjuvants; and U.S. Pat. No. 6,207,385 describes nucleic acids bound to dextran carrier macromolecules. T. M. Hansen, 2003 *IVD Technol.*, pp.35–40 describes fluorescent dextran conjugates for use in quantitative assays. International Patent Application No. WO00/07019 (10 Feb. 2000) describes methods for preparing water soluble cross linked conjugates.

U.S. Pat. No. 5,627,078, describes multivalent dextran reagents for use in precipitation tests. This multivalent reagent employs dextran with a MW of 10 kDa up to the solubility limit of about 2000 kDa, and preferably employs MW of 20 to 500 kDa. These reagents have a ratio of dextran:bound molecules of about 1:5 to 1:50. See, also, C. W. Cairo et al, 2002 *J. Am. Chem. Soc.* 123, 1615–19. These documents and those cited above are incorporated by reference to provide information on presently known aminodextrans and uses of same in aminodextran conjugates and other forms.

However, problems associated with the use of aminodextran conjugates include inconsistent yields and amplification that vary between preparation lots of the conjugates, and even from chromatographic fraction to fraction within a lot. The use of such inconsistent lots of the aminodextran polymer has resulted in less efficient labeling than desirable for diagnostic procedures involving cell labeling.

There thus remains a need in the art for methods and compositions that overcome the deficiencies of currently employed aminodextran conjugates, while retaining their useful qualities as cell labeling reagents.

SUMMARY OF THE INVENTION

In one aspect, the invention provides a composition comprising polydisperse aminodextran polymer molecules of a narrow size distribution, which composition is soluble in water or aqueous solutions. The polydisperse molecules present in the composition have a narrow size distribution characterized by an average molecule mean hydrodynamic diameter of greater than 115 nm, a polydispersity index of between 0.10 and 0.47, an average molecular weight (MW) greater than 3 million daltons, and an amine content of greater than 50 amines per molecule. Surprisingly even such compositions having an average molecular weight of greater than 7 MDa are soluble in water.

In another aspect, the invention provides a composition comprising a conjugate and a cell labeling reagent comprising the polydisperse aminodextran polymers of narrow size distribution described herein conjugated to a selected labeled protein or fluorescent protein.

In still another aspect, the invention provides a method for producing the cell labeling reagent/conjugate and the polydisperse aminodextran composition in which the aminodextran molecules have a narrow size distribution. The resulting compositions are soluble in aqueous solutions.

Other aspects and advantages of the present invention are described further in the following detailed description of the preferred embodiments thereof.

BRIEF DESCRIPTION OF THE DRAWINGS

FIG. 7A shows the consistency of results obtained when the improved aminodextran is used: the fractions yielded by the process are equivalent and the histograms generated can be overlayed.

FIG. 3B demonstrates that these two fractions of CD8B-Dex-PC5 are clearly not equivalent and thus are evident of a non-homogeneous product.

DETAILED DESCRIPTION OF THE INVENTION

Figure 1A:
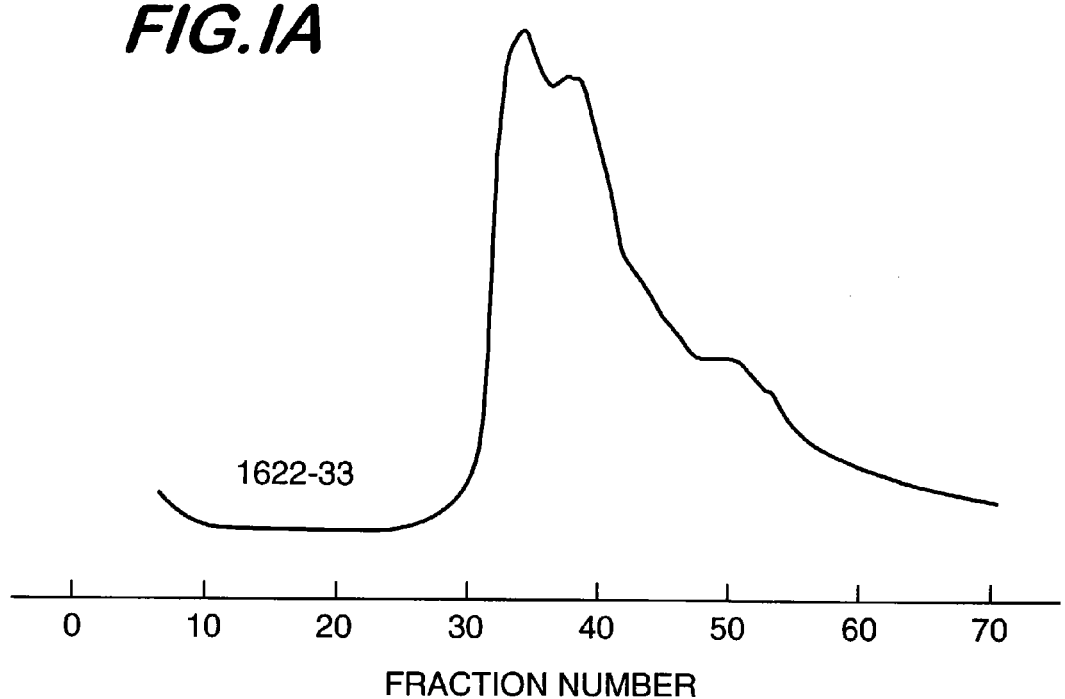
FIGS. 1A to 1D are graphs of chromatograms for three different lots of standard aminodextran available in the prior art or available by conventional synthesis, MP8, MP8-2, and MP8-3, and for aminodextran lot 1622–33, each chromatogram produced by a conventional fractionation column. The Y axis in each chromatograph is relative absorbance at 280 nm; the X axis in each chromatograph shows the fraction numbers from the column. See Example 1.
Figure 1B:
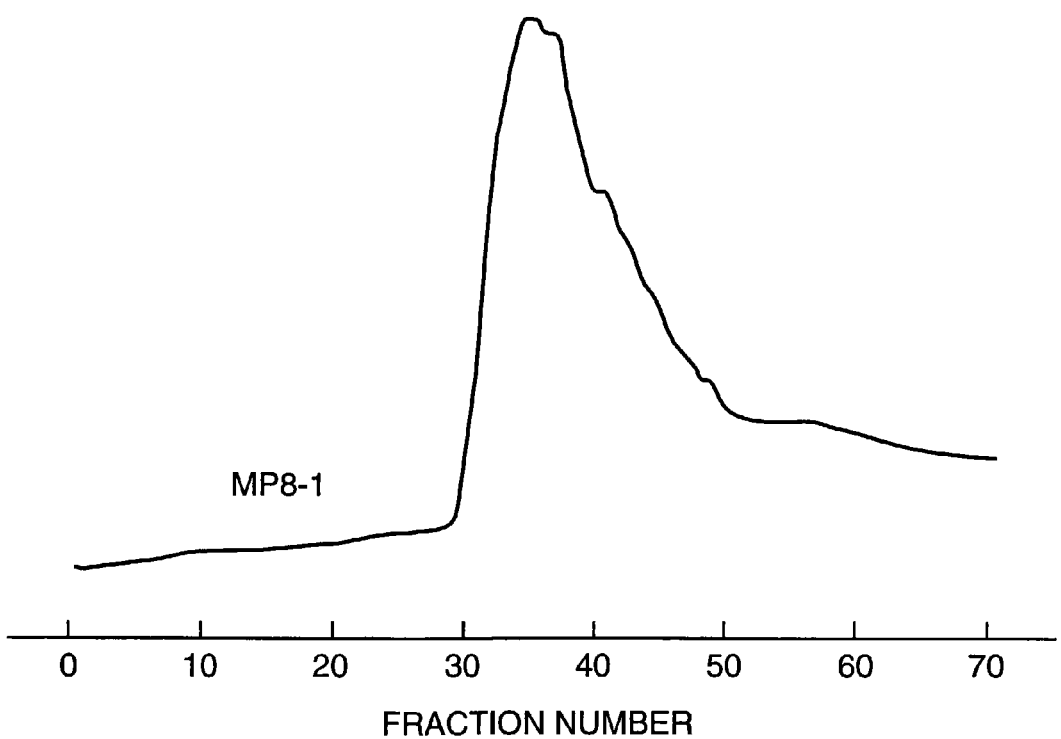
Figure 1C:
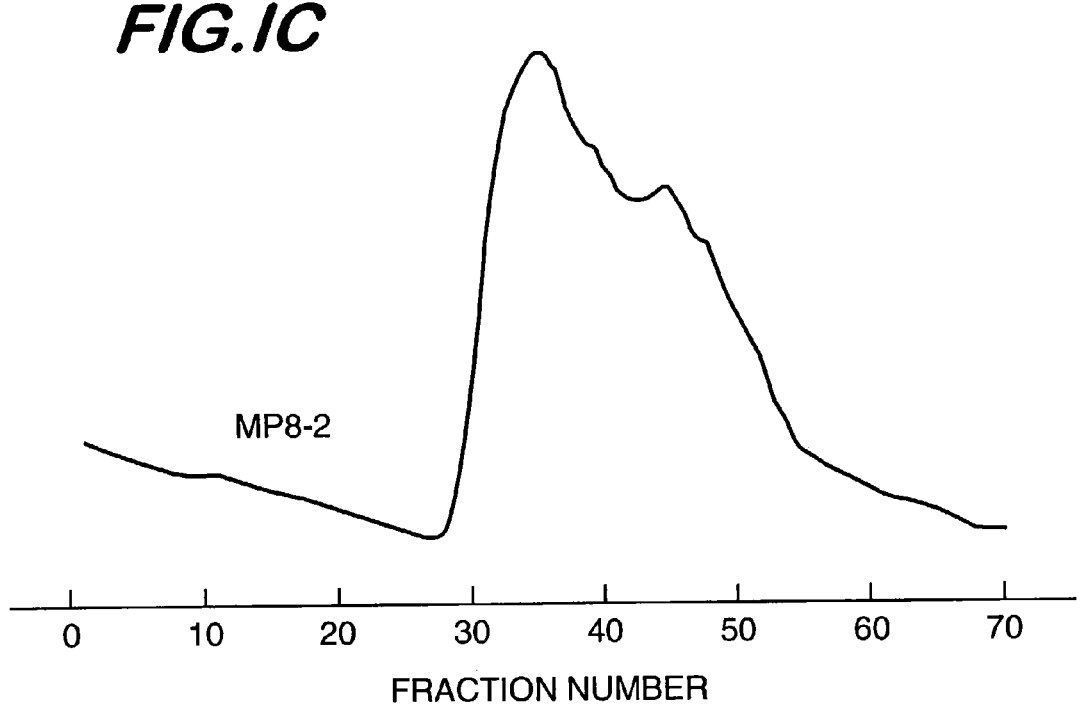
Figure 1D:
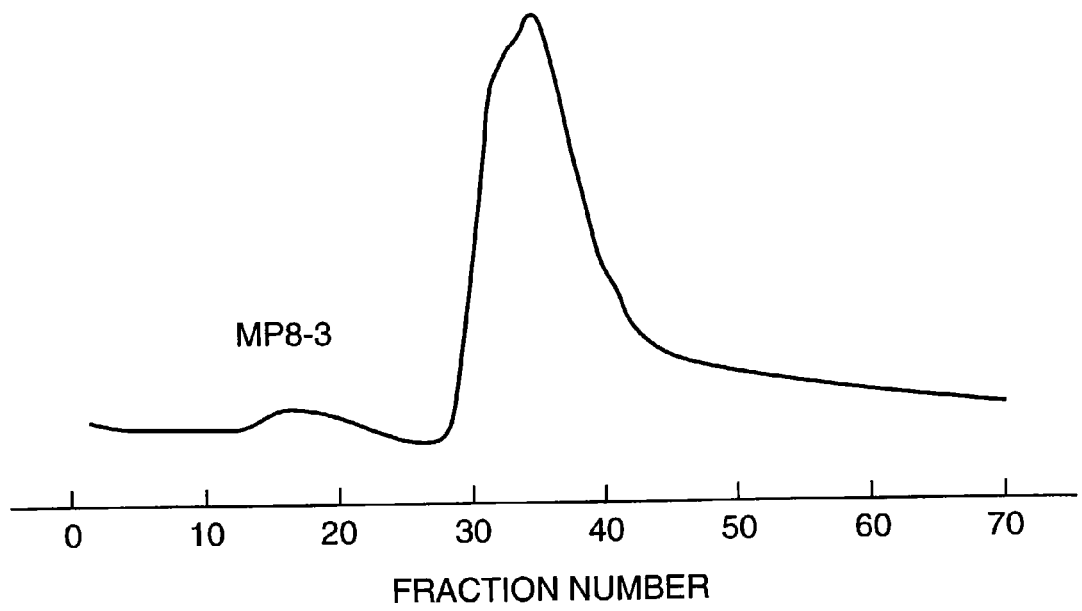

The inventors have determined that the aforementioned problems associated with use of aminodextran conjugates occur because aminodextran, whether supplied by a commercial vender or made by the inventor, consists of a highly heterogeneous mixture of molecular weights (MW) or chain lengths. For example, a typical aminodextran mixture contains polymer of mixed MW species, providing an average MW for the mixture of between about 25 kDa to a nominal 3,900 kDa. The polydispersity indices of these standard aminodextrans is greater than 0.40, as can be seen, for example, in Table 2 below. Also such aminodextran molecules in these standard mixtures had an average mean hydrodynamic diameter (i.e., 2× the radius of gyration×0.7) of less than about 115 nm, as can be seen in both Tables 1 and 2 below. Further some of the available nominally highest MW species of dextran tend to be only slightly soluble or insoluble in water. For example, commercially available industrial grade dextran (Sigma D 5501) of 5 to 40 MDa average MW is slightly soluble or insoluble in water or aqueous media.

The desired material for use as a conjugate is the highest MW aminodextran polymer possible, because the higher MW species contains more sites for activation and attachment of protein molecules, such as fluorescent proteins. The inventors determined that as presently prepared, after conjugation of proteins to the standard available aminodextrans, the lower MW conjugates are not completely separable from the desired highest MW conjugates. During use in labeling of biological cells, the lower MW chains are more mobile in solution and are much more numerous than the high MW chains. Therefore, cells become preferentially labeled with low MW material, resulting in lower fluorescence potential.

Having now identified the source of several of the problems associated with the use of aminodextran polymer, the present invention provides novel compositions, such as improved polydisperse aminodextran polymer compositions and conjugates and reagents containing same. These improved polymer compositions comprise only the higher MW polymer and therefore novel reagents are characterized by substantially all higher MW conjugates with an increased ability to conjugate with fluorescent (or other) proteins. Such high MW reagents thereby improve the diagnostic processes in which they are employed, because they remove the normal preference for the lower MW fractions of aminodextran to bind to cells before the higher MW fractions. With such an improved aminodextran composition containing high MW aminodextrans, the aminodextran conjugates with proteins and/or dyes are more homogeneous and bind with similar avidity to the cells. Further, and surprisingly, such high MW reagents are soluble in aqueous solution, as demonstrated in the examples below.

One aspect of this invention provides a composition comprising polydisperse aminodextran polymer molecules. The composition is soluble in an aqueous solution at a concentration of 10 mg/ml. The polydisperse aminodextran molecules in the composition have a narrow size distribution. By "narrow size distribution" as used herein is meant that the aminodextran molecules in the composition have an average molecule mean hydrodynamic diameter of greater than 115 nm, a polydispersity index of between 0.10 and 0.47, an average molecular weight (MW) greater than 3 million daltons, and an amine content of greater than 50 amines per molecule. In one aspect, the average MW of the polydisperse aminodextran composition is greater than 4 million. In another embodiment, the average MW is greater than 5 MDa. In another embodiment, the average MW is greater than 6 MDa. In still a further embodiment, the average MW is greater than 7 MDa. In still a further embodiment, the average MW is greater than 8 MDa. Such molecular weights may be conveniently measured by using one or more conventional techniques, such as the Triple Detector method employing refractive index, viscosity, and light scatter (Viscotek, Inc., Houston, Tex.); or the quasi-elastic light scattering (QELS) or photon correlation spectroscopy (PCS) as performed with the Coulter Model N4MD sub-micron particle analyzer; or particle electrophoresis as performed on the Coulter Doppler electrophoretic light scattering analyzer (DELSA).

This improved polydisperse aminodextran composition may also be characterized by solubility in water. In one embodiment, the composition of this invention is soluble in water at a minimum concentration of 10 mg/ml. In another embodiment, the composition is completely water soluble at concentrations of between about 10–50 mg/ml. In another embodiment, the composition's water solubility is at 20–40 mg/ml. Surprisingly, these improved polydisperse compositions retain their water solubility well above the average molecular weight of 3 million daltons. As demonstrated in the following examples, even an improved polydisperse composition of average MW of 8 MDa is water soluble. The improved aminodextran compositions of this invention represent the first dextran derivatives of high MW between 3 and 8 MDa to be soluble in water or aqueous media, and thus be useful as large polymeric carriers for protein molecules such as streptavidin, monoclonal antibodies, phycoerythrin and its tandem derivatives.

Still another characteristic of the improved polydisperse aminodextran compositions of the present invention, is that they contain an amine content of greater than 50 amines per aminodextran molecule. In another embodiment, the amine content of is approximately 70 amines per aminodextran molecule. In yet another embodiment, the amine content of is approximately 90 amines per aminodextran molecule. In still another embodiment, the amine content of is approximately 110 amines per aminodextran molecule. In another embodiment, the amine content of the improved Amdex of this invention is about 130 amines per aminodextran molecule. The amino content may be measured using the ninhydrin method (J. M. Stewart and J. D. Young, Solid Phase Synthesis of Polypeptides, ed. W. H. Freeman and Co., San Francisco, Calif. 1969, pp.57–58).

Still other characteristics of the improved aminodextran of narrow size distribution is that the average molecule mean hydrodynamic diameter of the molecules in the composition are greater than 115 nm. In one embodiment, the average molecule mean hydrodynamic diameter of the composition, measured as 2× the radius of gyration $R_g \times 0.7$, is greater than 125. In another embodiment, the average molecule mean hydrodynamic diameter of the composition is greater than 150.

An additional characteristic of the improved polydisperse aminodextran compositions of this invention is that these compositions each have a polydispersity index of between 0.10 and 0.47.

As used throughout this specification, the term "improved aminodextran" or "purified aminodextran" means the aminodextran compositions of this invention characterized by a narrow distribution of MW, a polydispersity, an amino content and solubility as described above.

In one embodiment, these high MW aminodextran compositions may be prepared by a process involving the purification of polydisperse, high MW aminodextran polymer molecules from the currently available wide size distribution mixtures of aminodextran polymers having average MWs ranging from 34.4 kDa to 3,911 kDa, as shown, e.g., in Table 1 below. Both commercially supplied and synthesized aminodextran were found to have such wide molecular weight distribution. The dextran (Sigma or Pharmacia) that is used as raw material to prepare aminodextrans has a wide distribution in MW. For example, a product that the commercial suppliers state has a nominal average MW of approximately 2 mDa could contain MW mixtures ranging from 0.5 to 3.9 mDa. The reaction conditions for amination of dextran can also result in partial chain degradation. Higher amine content product is more chain degraded. Reaction conditions must be adjusted to provide adequate amine content to allow proteins, e.g. streptavidin and phycoerythrin, to be bound in saturation amounts, while maintaining the highest possible MW to also allow sufficient amplification of signal. The starting material, dextran, is normally 2–3 million g/mol (T-2M), and is still water soluble. This grade is available from commercial sources, such as Sigma and Pharmacia.

Such wide size distribution mixtures of aminodextran may be purchased commercially, from e.g., Molecular Probes (lot MP8), or prepared by conventional reactions using a carboxymethylation step and an amination step. The particular method of making the wide size distribution compositions of aminodextrans is not limited to such techniques and it is envisioned that any technique for making such wide size distribution compositions of aminodextrans is within the practice of the invention. These mixtures are generally prepared by varying the starting dextran and the amination conditions. See, e.g., U.S. Pat. No. 5,466,609 and U.S. Pat. No. 5,527,713. The highest molecular weight known for these heterogeneous compositions is a nominal average MW of 2–3 MDa, with polydispersity indices of 0.40 or higher and average mean hydrodynamic diameter of lower than 115 nm.

Thus the production method for the improved aminodextran compositions of this invention involves separating from a first mixture of polydisperse aminodextran particles of a wide size distribution characterized by an average molecule mean hydrodynamic diameter of less than 115 nm, and a polydispersity index greater than 0.4, a second mixture of polydisperse aminodextran polymer molecules having a narrow size distribution characterized by an average molecule mean hydrodynamic diameter of greater than 115 nm, a polydispersity index of between 0.10 and 0.47, an average molecular weight (MW) greater than 3 million daltons, and an amine content of greater than 50 amines per molecule. The second mixture of separated molecules is soluble in an aqueous solution at a concentration of 10 mg/ml and can be lyophilized for storage. If lyophilized, these improved aminodextran compositions may be redissolved in an aqueous solution, such as an aqueous sodium nitrate solution. Following the redissolving, optional measurements, e.g., light scattering as described above, may be performed to verify the characteristics of the improved compositions.

The process of the present invention for preparing improved polydisperse aminodextran compositions of narrow size distribution involves separation steps suitable for filtration or fractionation of high molecular weight dextrans from the low molecular weight species in conventional aminodextran mixtures. For example, the inventors employed fractionation by gel filtration or size exclusion column chromatography. The use of size exclusion column chromatography or gel filtration enables successful isolation of the high molecular weight fractions of interest. Similarly commercial scale processes are anticipated to provide the same results. While the following examples employ agarose gel materials in the chromatography column (which has been found particularly desirable for conjugates with phycoerythrin), other gel filtration media may be used. An example of useful agarose beads is commercially available from e.g., Amersham Pharmacia Biotech, under the mark SEPHAROSE 4B™ or SEPHAROSE 2B™, or from Bio-Rad Laboratories under the mark BIOGEL™ A15m. Among useful gel filtration materials are sold under the trademarks SEPHACRYL S-400™, S-500™ or S-1000™, and SUPEROSE 6™ (Amersham Biosciences Corp.). This purification method is not limited by the particular methodology used to separate the high MW aminodextrans from the low MW species. Similarly, it would be possible to employ known systems of analytical centrifugation to accomplish the same purification (see, e.g., J. L. Cole, 1999 *J. Biomolec. Tech.* 10:163). Another useful method is field flow fractionation, such as described in J. C. Giddings, 1993 *Science,* 260:1456.

In one embodiment, heterogeneous mixtures of aminodextran polymers of a wide distribution of various MWs, such as the commercially sold Amdex MP8, are passed over a chromatographic column of 4% agarose gel beads. The earliest chromatographic fractions, corresponding to the narrow distribution of high MW aminodextran molecules, are identified, and pooled as they elute from the column. These fractions are conventionally desalted and lyophilized. Generally, about the earliest one-third of the material by volume comprises the high MW portion of the aminodextrans useful in the invention. Use of this material results in uniform, high amplification, high yield conjugates suitable for use as cell markers for flow cytometric analysis.

As described in more detail in the Examples below, the inventors' method for purifying the higher MW aminodextran from the heterogeneous mixture results in improved compositions that, unlike the heterogeneous mixtures containing a wide distribution of aminodextran including many low molecular weight fractions of the heterogeneous aminodextran, avoid interference in interactions with potential cellular targets. The improved aminodextran of this invention provides a more homogeneous product conjugate of narrow size distribution and fixed number of protein molecules (e.g., labels or markers) per aminodextran molecule. Further, the larger aminodextran of narrow size distribution present in the improved aminodextran compositions of this invention allow greater numbers of detectable protein to conjugate with the aminodextran. Such conjugates can provide larger fluorescence amplification ratios for targeted cells in flow cytometry, as shown in the Examples below.

The low MW polymer fragments of the aminodextran compositions of the prior art are much more numerous on a molar basis and have higher mobility in the labeling of cells and therefore react preferentially with target sites. As illustrated in the comparative examples below, the small, low MW fragments have a low phycobiliprotein (e.g., phycoerythrin) content giving low fluorescence amplification. In contrast, using purified high MW aminodextran according to this invention, permits the separations of the conjugate from excess PE and streptavidin (SA) to be well defined and reduces the loss of PE and SA into the low MW aminodextran fragments. The separation of the high MW aminodextran from the low MW ranges of the commercially available aminodextran compositions as described by this invention also removes any contaminating microbial proteins, such as endotoxins, which may have been formed in the dextran fermentation production.

The improved high MW aminodextran compositions of this invention are useful in preparing the reagents, particularly cell labeling reagents for which aminodextrans have a known use. For example, a composition of this invention includes a conjugate comprising the improved soluble polydisperse aminodextran molecules described above, conjugated to a selected labeled protein. Such a labeled protein can be a fluorescent protein or a protein labeled with a fluorescent protein as described below. The cell labeling reagent can further be described as comprising polydisperse aminodextran polymer molecules, soluble in an aqueous solution at a concentration of 10 mg/mL. The dextran molecules of the composition have a narrow size distribution characterized by an average molecule mean hydrodynamic diameter of greater than 115 nm, a polydispersity index of between 0.10 and 0.47, an average molecular weight (MW) greater than 3 million daltons, and an amine content of greater than 50 amines per molecule. These dextran molecules are conjugated via the amines to selected labeled proteins. For example, these improved aminodextran compositions can be conjugated with detectable markers for use in flow cytometric analyses. Phycobiliproteins, tandem dyes, certain fluorescent proteins, small chemical molecules, and certain molecules detectable by other means can all be considered markers for flow cytometry analyses. See, e.g., the markers listed in *Handbook of Fluorescent Probes and Research Chemicals,* 6th Ed., R. P. Haugland, Molecular Probes, Inc., Eugene, Oreg. (1996).

"Phycobiliproteins" are a family of macromolecules found in red algae and blue-green algae. The biliproteins (the term "biliproteins" is equivalent to the term "phycobiliprotein") have a molecular weight of at least about 30,000 daltons, more usually at least about 40,000 daltons, and may be as high as 60,000 or more daltons usually not exceeding about 300,000 daltons. The biliproteins will normally be comprised of from 2 to 3 different subunits, where the subunits may range from about 10,000 to about 60,000 molecular weight. The biliproteins are normally employed as obtained in their natural form from a wide variety of algae and cyanobacteria. The presence of the protein in the biliproteins provides a wide range of functional groups for conjugation to aminodextran molecules. Functional groups that are present include amino, thiol, and carboxyl. Examples of phycobiliproteins useful for conjugation with the aminodextran of the present invention are phycocyanin, allophycocyanin (APC), allophycocyanin B, phycoerythrin (PE) and preferably R-phycoerythrin. The tandem dyes are non-naturally occurring molecules that may be formed of a phycobiliprotein and another dye. See, for example, U.S. Pat. No. 4,542,104 and U.S. Pat. No. 5,272,257. Examples of tandem dyes useful in the present invention are phycoerythrocyanin or PC5 (PE-Cy5, phycoerythrin-cyanin 5.1: excitation, 486–580 nm, emission, 660–680 nm) (A. S. Waggoner et al, 1933 Ann. N.Y. Acad. Sci., 677:185–193 and U.S. Pat. No. 5,171,846) and ECD (phycoerythrin-texas red; excitation, 486–575 nm, emission, 610–635 nm) (U.S. Pat. No. 4,542,104 and U.S. Pat. No. 5,272,257. Other known tandem dyes are PE-Cy7, APC-Cy5, and APC-Cy7 (M. Roederer et al, 1996 Cytometry, 24:191–197). Tandem dyes, PC5 and ECD, have been successfully directly conjugated to aminodextran by several methods that involve iminothiolane activation of the dye.

Still other markers may be directly conjugated to the improved aminodextran of this invention. Examples of such markers are fluorescein isothiocyanate (FITC), the green fluorescent proteins and blue fluorescent proteins. Others are listed in the Handbook cited above. The biliproteins and tandem dyes are commercially available from various sources including Coulter International Corporation, Miami, Fla., Molecular Probes, Inc., Eugene, Oreg. and Prozyme, Inc., San Leandro, Calif. The other markers or labels discussed above may be obtained commercially from known sources. Preferably, the fluorescent light emission is measured by flow cytometric analysis.

Similarly, the improved compositions of high MW aminodextran can be conjugated with antibodies, by known methods, also for the purposes of cell labeling.

Thus, these improved aminodextran compositions of this invention may be useful in methods for preparing a variety of conjugates useful as cell labeling reagents for flow cytometry. For example, antibody-aminodextran-phycobiliprotein conjugates or other similarly labeled conjugates, e.g., streptavidin-aminodextran-phycobiliprotein conjugates, may be prepared using the narrow MW distribution aminodextran compositions of the invention. Such methods employ known techniques for making such conjugates, including steps described in detail in the examples and summarized herein. Such steps include activating a selected antibody (e.g., to a cell surface antigen on a selected cell) with iminothiolane, then purifying the activated antibody. The phycobiliprotein may similarly be activated with iminothiolane, and then purified. The activated and purified antibody and phycobiliprotein are reacted. The improved aminodextran of the present invention is activated with sulfo-SMCC, then purified. A reaction is caused by mixing all activated components together for about 16–24 hours; and thereafter the mixture is purified into its components, by, e.g., size exclusion chromatography. Still other methods for generating such conjugates are taught in the above-referenced patent literature.

According to another aspect, the purified or improved aminodextran of the present invention may be used in methods for detecting biological substances in a variety of known assays. One exemplary embodiment of such a method includes the steps of mixing an antibody-aminodextran phycobiliprotein conjugate with a sample containing a substance to be detected, to allow the antibody of the conjugate to bind to the substance to form a complex. Each phycobiliprotein molecule of the complex may thereafter be excited, to cause it to fluoresce. Fluorescence may be caused by excitation radiation in order to obtain a fluorescence signal from the complex. Thereafter, the fluorescent signal from the complex is detected.

Thus, the conjugates of the present invention may be used in a wide variety of ways, such as those described in the documents cited in the background of this specification. For example, for enhancing known methodologies for the detection, diagnosis, measurement and study of antigens, either present as individual molecules or in more complex organizations, such as viruses, cells, tissue, organelles, e.g. plastids, nuclei, etc. Among the preferred "substances" to be detected by methods such as this are hematological cells and particles using flow cytometry. Another use of the subject conjugates is in immunoassays or competitive protein binding assays, where the subject biliproteins serve as fluorescent labels. Here, the biliprotein conjugate may be conjugated to either a ligand or a receptor, preferably an antibody.

For other uses, as well as for other proteins with which the improved aminodextrans can be associated, see e.g., U.S. Pat. Nos. 5,527,713; 5,658,741; 5,891,741; 5,945,293; 5,994,089; 6,074,884 and 6,387,622: among others, as well as O. Siiman et al, 1999 Bioconj. Chem., 10(6):1090–1106. These patents and publications are incorporated by reference herein for the purposes of teaching known methods and compositions for using aminodextrans. All such methods and uses are enhanced by the use of the improved aminodextran compositions of this invention, in place of the standard heterogeneous aminodextran compositions known and available to the art.

EXAMPLES

These examples demonstrate the use of the methods and compositions of the invention and the analysis thereof. The data reported in these Examples demonstrates that the improved compositions and methods of this invention are useful as cell labeling reagents and have performance parameters that permit improved analysis of samples. These examples are illustrative and do not limit the scope thereon. One of skill in the art will appreciate that although specific reagents and conditions are outlined in the following examples, modifications as described above can be made to provide the compositions of this invention or processes for use thereof.

Example 1

Preparation of High Molecular Weight Improved Aminodextran

A. Production of Aminodextran

Several lots of heterogeneous mixtures of aminodextrans of nominal molecular weight, 2M Da, were obtained from Molecular Probes, Inc. (MP8, MP8-2 and MP8-3). Additionally, the inventors produced their own aminodextran preparations, lot 9–85, and lots 1622–29 and 1622–33, using dextran of nominal molecular weight, 2M Da, supplied by Sigma and Pharmacia, respectively. The production process was as follows:

11.6 g chloroacetic acid, sodium salt is dissolved in 100 ml water, added to a solution of 11.2 g dextran with a MW of 2 MDa in 36 ml 1 M NaOH and stirred for 20 hours at 40° C. Afterwards the pH is adjusted to a value of 4 with 1M HCl and concentrated to a volume of 50 ml on a rotary evaporator. The carboxymethyldextran which forms is dissolved in 50 ml 2M ethylenediamine dihydrochloride, pH 5 and 3 g N-ethyl-N'(3-dimethylaminopropyl)carbodiimide monohydrochloride is added in portions within 60 minutes. It is stirred for a further three hours at room temperature at a constant pH value of 4.7, whereby 1M aqueous NaOH or 1M aqueous HCl solution is added by means of a titrator. The product is twice dialyzed against deionized water and subsequently lyophilized.

B. Purification

Aminodextran was purified according to the method of this invention using commercial column media, such as BIOGEL™ A15 m (BioRad), SEPHAROSE™ 4B (Amersham Biosciences) or ABT 4% gel (Agarose Bead Technologies). Fractions collected under the first eluted band, as measured by UV monitor (absorbance at a wavelength of 280 nm, Uvicord S or SII, Amersham Biosciences) and chart recorder (BD41, Kipp & Zonen), were pooled (fractions containing highest molecular weight material), concentrated, and used in conjugations of proteins.

Initial runs were performed at a scale of 100 mg aminodextran-MP8, separated on a small column (2.5 cm×48 cm), and the resulting first ⅓ peak fractions pooled and concentrated. The concentrate was assumed to contain 30 mg aminodextran, and was split into two equal portions, so that an assumed 15 mg of aminodextran was used for each conjugation.

A larger scale purification of 1.00 g aminodextran-MP8 was done on a column packed with SEPHAROSE 4B (2 L, 7.5 cm×40 cm). Fractions of the first ⅓ peak in the broad, first band eluted with 1×PBS from the column were concentrated, desalted by repeated washings with DI water in Centri-Prep tubes, and freeze-dried to yield 0.12 g of purified aminodextran as a white solid. Chromatograms for three trials of three different lots of aminodextran, MP8, MP8-2, and MP8-3, and for aminodextran lot 1622–33 are shown individually in FIGS. 1A–1D.

Fractionation on a 100 mg scale on a small column, collecting 3.8 ml per fraction, gave the high MW material in fraction numbers 18–22. Fractionation on the 2 L column at a 1.00 g scale, collecting 20 ml fractions, gave the high MW material in fractions 30–39.

Example 2

Triple Detector Results for High Molecular Weight Aminodextrans

The commercial heterogeneous mixtures of aminodextran identified above were sent for measurement of weight-average molecular weight, intrinsic viscosity, and refractive index in aqueous media to a commercial company, i.e., Viscotek, Inc. Also, the purified aminodextrans from lots MP8 and 1622–33, chromatographed on Sepharose 4B and selecting the high molecular weight fractions for subsequent lyophilization, as described in Example 1 were also subjected to the same triple detector measurements. The data are summarized in Table 1.

TABLE 1

Triple Detector System Data for Aminodextran Compositions

| Lot No. | $M_w$, kDa | $Log(M_w)$ | $IV_w$, dL/g | $Log(IV_w)$ | $R_g$, nm | $Log(R_g)$ |
|---|---|---|---|---|---|---|
| MP8 | 2,734 | 6.437 | 0.774 | −0.111 | 45.75 | 1.660 |
| 9-85 | 2,331 | 6.367 | 0.710 | −0.149 | 42.15 | 1.625 |
| 1622-29 | 3,137.5 | 6.496 | 0.796 | −0.0991 | 48.37 | 1.684 |
| MP8-2 | 2,176 | 6.338 | 0.656 | −0.183 | 40.12 | 1.603 |
| 1622-33 | 3,911 | 6.592 | 0.782 | −0.107 | 51.75 | 1.714 |
| MP8, purif | 7,999 | 6.903 | 0.939 | −0.0273 | 69.63 | 1.843 |
| 1622-33, purif | 6,887 | 6.838 | 0.867 | −0.0620 | 64.50 | 1.809 |
| MP130 | 2,999 | 6.477 | 0.674 | −0.171 | 41.3 | 1.616 |
| 5X-Amdex, lot-11 | 414 | 5.617 | 0.262 | −0.582 | 15.6 | 1.193 |
| 5X-Amdex, lot-11 | 25.6 | 4.408 | 0.0602 | −1.22 | 3.79 | 0.579 |
| 1X-Amdex, lot-75 | 1,044 | 6.019 | 0.442 | −0.355 | 25.2 | 1.401 |
| 1X-Amdex, lot-75 | 93.9 | 4.973 | 0.205 | −0.688 | 8.80 | 0.944 |
| Dextran, T-2M | 2,102 | 6.323 | 0.609 | −0.2 | 35.5 | 1.550 |
| 5X-Amdex, lot1-5 | 70.0 | 4.845 | 0.167 | −0.785 | 7.38 | 0.868 |
| 5X-Amdex, lot1-5 | 34.4 | 4.537 | 0.100 | −1 | 4.96 | 0.695 |
| 5X-Amdex, lot-69 | 69.95 | 4.845 | 0.141 | −0.851 | 7.06 | 0.849 |
| 5X-Amdex, lot11-6 | 44.5 | 4.648 | 0.0999 | −1 | 5.40 | 0.732 |
| 5X-Amdex, lot2-2 | 168.4 | 5.226 | 0.186 | −0.73 | 10.35 | 1.0149 |

This triple detector data on two samples of purified aminodextran of this invention, i.e., MP8 and lot 1622–33, showed very high average MWs of 8.0 and 7.0 MDa, respectively. The results of the additional data were then added to the Mark-Houwink plots of log(intrinsic viscosity, $IV_w$) versus log(weight average molecular weight, $M_w$) and log(radius of gyration, $R_g$) versus $log(M_w)$ for aminodextrans (Aminodextran-MP, 1X-Aminodextran, and 5X-Aminodextran) having a wide range of molecular weight between 25 and 3,900 kDa. See FIGS. 2 and 3, which contain both old and new data. The new data appear on FIGS. 2 and 3 as points to the furthest right-hand-side, in the 6–7 range of $log(M_w)$.

Figure 2:
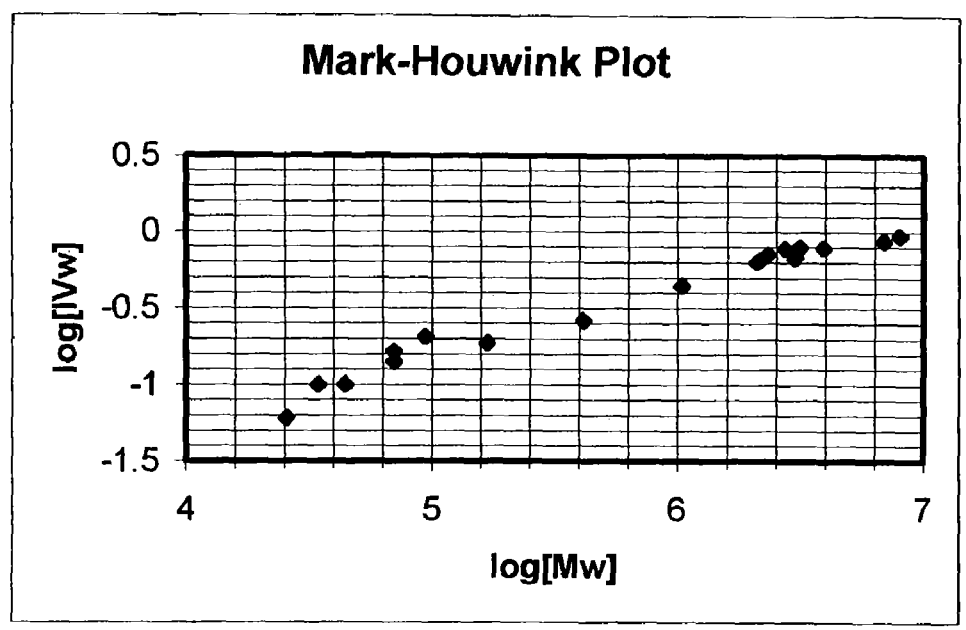
FIG. 2 is a Mark-Houwink plot of $\log(IV_w)$ versus log $(M_w)$ that had been previously described in O. Siiman et al, 1999 *Bioconjugate Chem.*, 10(6), 1090–1106, incorporated by reference, for aminodextrans with a wide range of molecular weight between 25 and 3,000 kDa (e.g., Amdex-MP, 1X-Amdex, and 5X-Amdex). This plot is modified from its appearance in the publication by the addition of new data. The new data appear on FIG. 2 as points to the furthest right-hand-side, in the 6–7 range of $\log(M_w)$. This data is discussed in Example 2 below.
Figure 3:
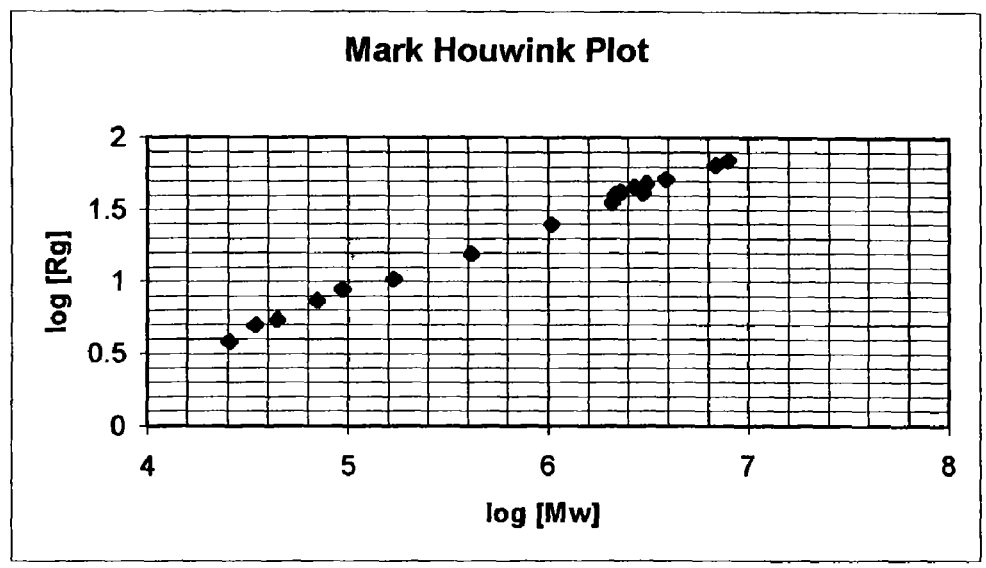
FIG. 3 is a Mark-Houwink plot of $\log(R_g)$ versus $\log(M_w)$ for various aminodextrans and dextran. New data appear on FIG. 3 as points to the furthest right-hand-side, in the 6–7 range of $\log(M_w)$. This data is discussed in Example 2 below.
Figure 4A:
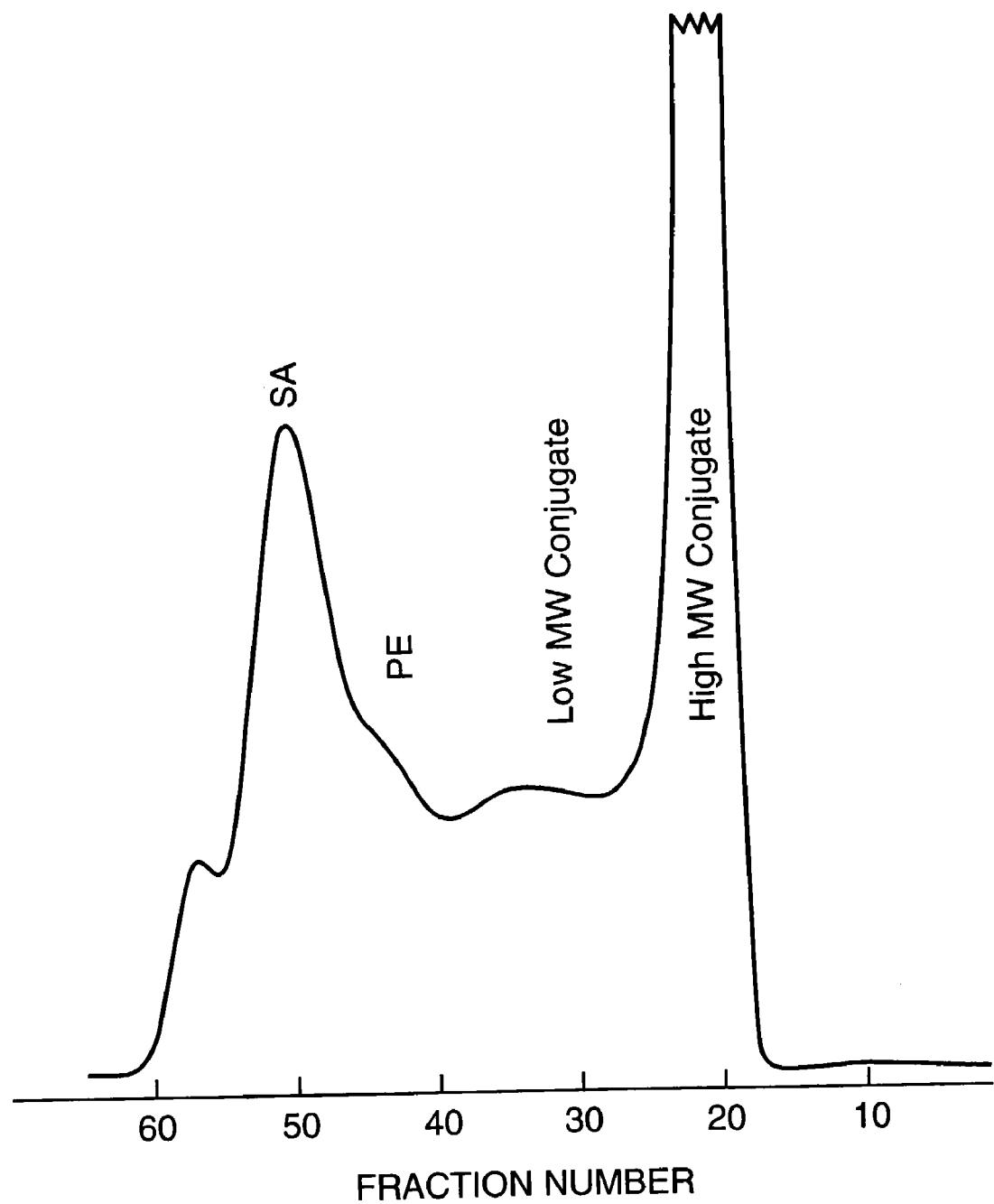
FIG. 4A is a chromatogram produced from applying the streptavidin (SA)-aminodextran-phycoerythrin conjugate made with conventional aminodextran on a fractionation column. Note that there is a very broad peak at about fraction number 20–40 which contains considerable low MW conjugate.
Figure 4B:
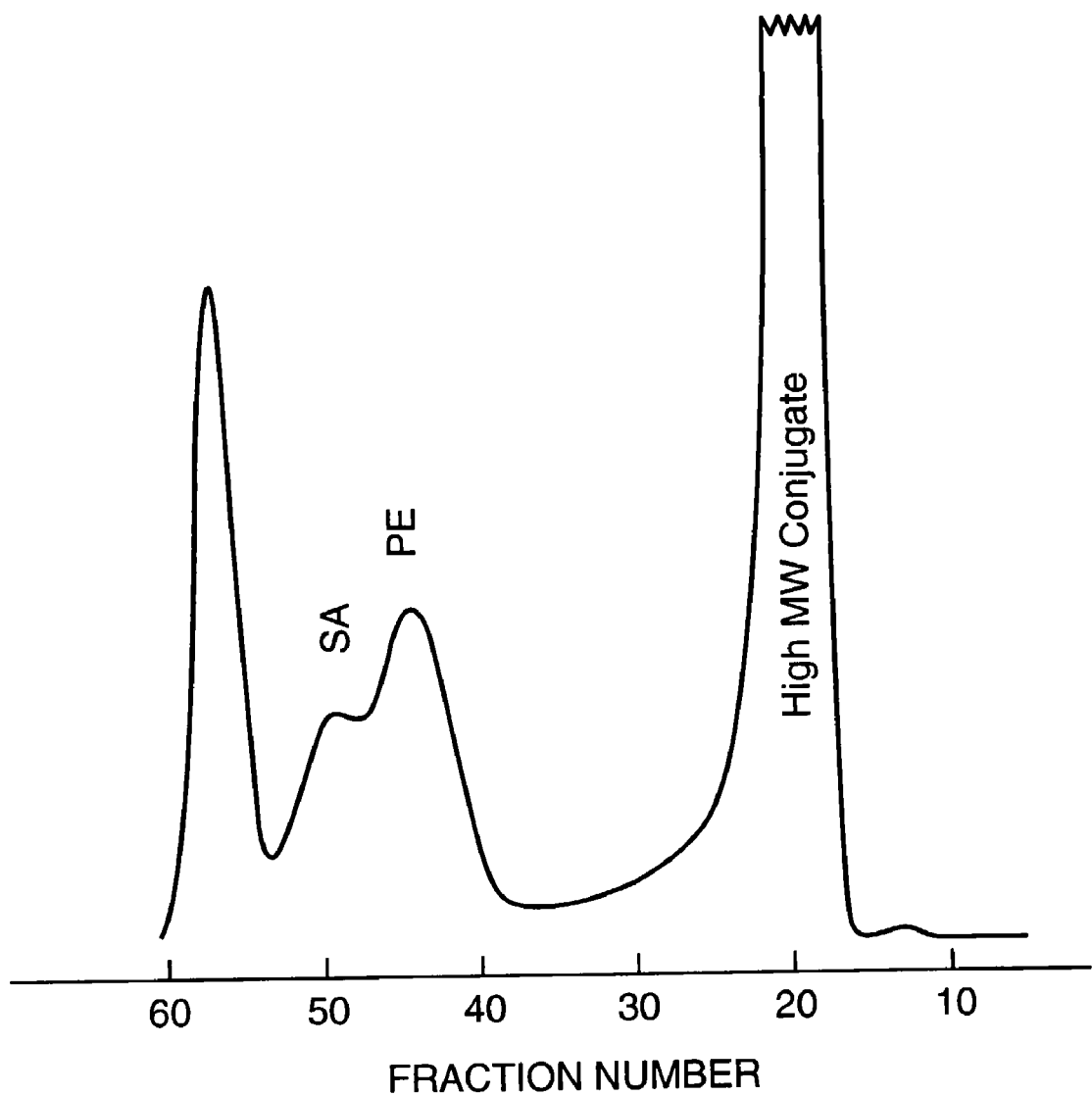
FIG. 4B is a chromatogram produced from applying the streptavidin (SA)-aminodextran-phycoerythrin (PE) conjugate made with the inventors' purified, polydisperse aminodextran of narrow size distribution (also referred to as "improved Amdex") on a fractionation column. Note that there is a very narrow, homogeneous peak at about fraction number 20 that contains the high MW conjugate.
Figure 5A:
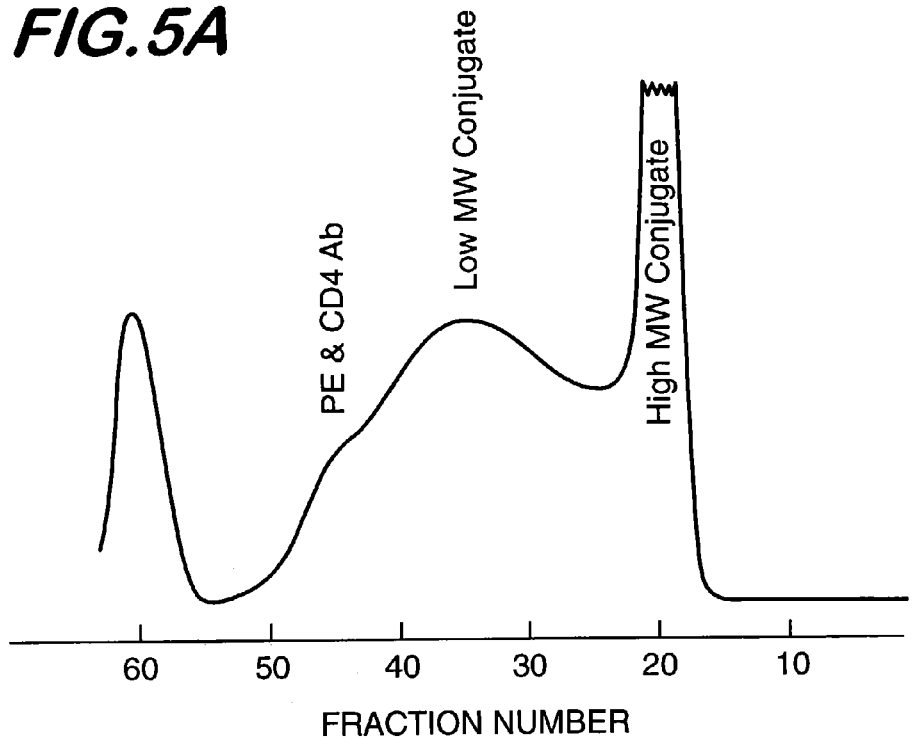
FIG. 5A is a chromatogram produced from applying CD4 antibody (CD4 Ab)-aminodextran-phycoerythrin (PE) conjugate made with conventional aminodextran on a fractionation column. Note that there is a very broad peak at about fraction number 22–40 which contains considerable low MW conjugate.
Figure 5B:
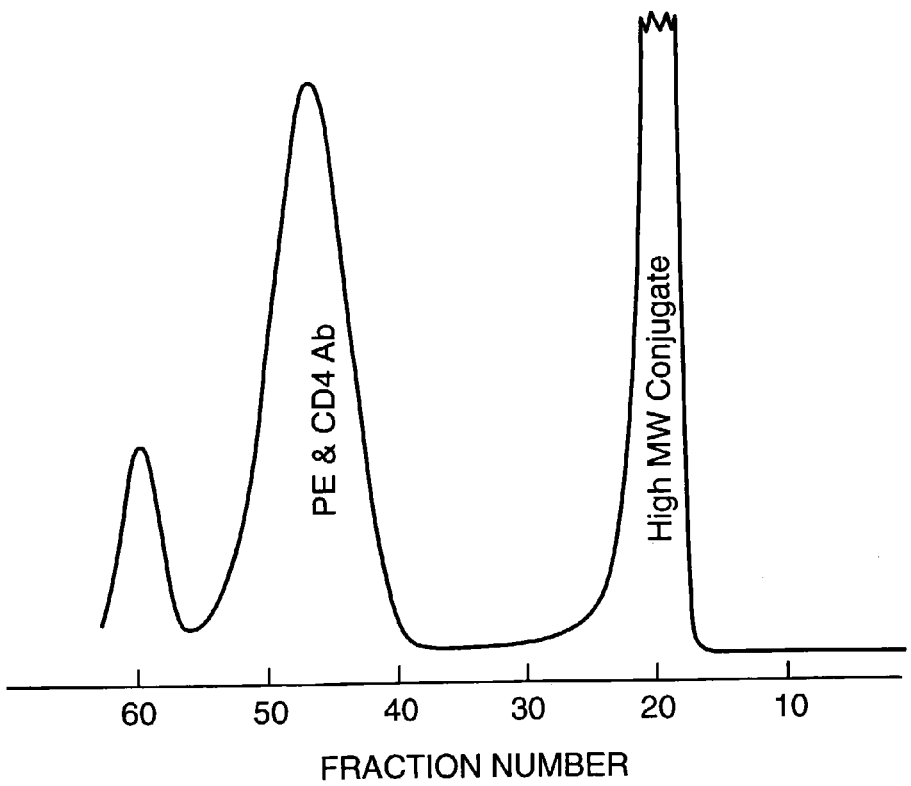
FIG. 5B is a chromatogram produced from applying the CD4 antibody (CD4 Ab)-aminodextran-phycoerythrin (PE) conjugate made with the inventors' purified, polydisperse aminodextran of a narrow size distribution on a fractionation column. Note that there is a very narrow, homogeneous peak at about fraction number 18–21 which contains the high MW conjugate.

The log-log plots in FIGS. 2 and 3 suggested that the very high MW aminodextrans were related. The high molecular weight data between $10^6$ and $10^7$ Da show slopes of 0.21 and 0.40, respectively, in the two plots. The two graphs may be analyzed in terms of three regions of differing slope: 1) FIG. 2 shows slopes of 0.46 and 0.80 in the intermediate 5.2 to 6.2 region and far left hand side region; 2) FIG. 3 shows slopes of 0.48 and 0.65 in similar regions. The high MW aminodextrans show very little change in size of aminodextran with increasing MW, indicating a more dense, compact random coil structure compared to aminodextrans in the intermediate region, of slope about 0.50, which has been associated with random coil, linear chain polysaccharide. Further, native dextran (E. Antonini et al., 1964 *Biopolymers* 2: 27: L. H. Arond and H. P. Frank 1954 *J. Phys. Chem.* 58, 953), a 15% syrup containing water-soluble dextran of about 10–30 MDa, is commercially available (Amersham Biosciences). Commercially available industrial grade dextran (Sigma D 5501) of 5 to 40 MDa average MW is only slightly or insoluble in water or aqueous media. The above aminodextrans represent the first dextran derivatives of high MW between 3 and 8 MDa to be completely soluble in water or aqueous media at a minimum concentration of 10 mg/ml, and thus be useful as large polymeric carriers for protein molecules such as streptavidin, monoclonal antibodies, phycoerythrin and its tandem derivatives.

Example 3

Dynamic Light Scattering Results for High Molecular Weight Aminodextrans

Quasi-elastic light scattering (QELS) measurements were performed on dilute (~1 mg/mL), buffered (1×PBS) solutions of the sulfo-SMCC derivatives of aminodextrans (MP8, MP8-2, and MP8-3) before and after purification with the COULTER® Model N4MD sub-micron particle analyzer. The sulfo-SMCC derivatives were measured since these are the molecular species present in solution immediately before conjugation with the activated proteins. Also, they are neutral in aqueous solution unlike the positively-charged aminodextrans in 1×PBS at pH 7.2–7.3. Results of unimodal analyses at a 90° scattering angle, including average mean hydrodynamic diameter, inter-assay standard deviation (SD), and polydispersity index are displayed in Table 2.

TABLE 2

Dynamic light scattering data for various sulfo-SMCC-aminodextrans

| Sulfo-SMCC derivative | Average mean hydrodynamic diameter, nm | Inter-assay SD, nm | Polydispersity index |
| --- | --- | --- | --- |
| MP8 | 104 | 2.4 | 0.40 |
| MP8-2 | 115 | 3.7 | 0.52 |
| MP8-3 | 75.6 | 2.5 | 0.54 |
| MP8 purified | 128 | 1.7 | 0.29 |
| MP8-2 purified | 153 | 1.9 | 0.40 |
| MP8-3 purified | 118 | 1.4 | 0.39 |

The polydispersity index [see, for example, B. B. Weiner, "Twenty seven years of QELS: A review of the advantages and disadvantages of particle sizing with QELS" in "Particle Size Analysis", N. G. Stanley-Wood and R. W. Lines, eds., The Royal Society of Chemistry, Cambridge, UK, 1992] is defined as the relative second moment ($\mu_2/\Gamma^2$) from cumulant analysis of the autocorrelation function collected in unimodal analysis. The higher mean hydrodynamic diameters greater than 100 nm compared to static light scattering measurements, large intra-assay standard deviations of about 47–57 nm, and polydispersity index values greater than 0.1, all point to the presence of aggregates in the suspensions of aminodextran in 1×PBS. A polydispersity index of between 0.0 and 0.1 is considered to indicate a unimodal size distribution. Index values ranging from 0.1 to 1.0 are believed to show a wide size distribution or a multi-modal size distribution. SDP intensity analyses appear to indicate a bimodal distribution when 90° light scattering was used and a trimodal distribution (including a 1–5 micron diameter component that was missed at 90°) when low angle 22.8° light scattering was used.

Example 4

Synthesis of Streptavidin-Aminodextran-Phycoerythrin Conjugates

Ternary conjugates for cell labeling were formed by sequential conjugation of aminodextran with a phycobiliprotein, such as PE, PC5 or ECD, then introducing streptavidin, CD4 and CD8β antibodies to form antibody-aminodextran-PE, -PC5, and -ECD conjugates.

A. Column Preparations

For the PE concentrate, a Sephadex G-50(fine) (Amersham Biosciences Cat. No. 7-0042-02) agarose gel was employed to pack a column (1.5 cm×28 cm). The G-50 gel was previously swelled in DI water.

Three additional G-50 columns (1.5 cm×28 cm) were prepared as above and equilibrated with PBS-EDTA (prepared by dissolving 0.75 g Disodium EDTA:2H$_2$O in 1 L PBS), prior to use as described below.

Another column used in the following procedures was made by pouring Sepharose 4B (Amersham Pharmacia Biotech AB, Cat. No. 17-0120-01) agarose gel into a 2.5 cm×50 cm column until the bed was packed to ~48 cm. The column was washed with PBS or PBS-0.1% NaN3 until the eluant had the conductivity reading equal to PBS (~15 mS).

B. Preparation of Phycoerythrin (PE) Concentrate

PE Storage Buffer was prepared as follows: To 950 ml of deionized (DI) water, was added 3.40 g potassium dihydrogen phosphate (CMS lot M246KETD), 4.35 g dipotassium hydrogen phosphate (CMS lot M244KENN) and 0.75 g disodium EDTA:2H$_2$O (EM Science lot 33238338). This mixture was stirred until salts were dissolved, and the pH adjusted to 7.00 with 50% potassium hydroxide (KOH; about 50 µl) and Q.S. to 1.00 L.

The PE buffer exchange is then performed by roller mixing a bottle of R-Phycoerythrin (R-PE; Prozyme, Inc., San Leandro, Calif.; lot 291, 053) containing 20 mg/ml for 30–60 minutes. R-PE (2.5 ml) was pipetted into each of four 50 ml disposable centrifuge tubes and each tube was diluted with 25 ml PE Storage Buffer (total PE=200 mg). Roller mix aluminum foil covered the tubes for 30 minutes. Then the tubes were centrifuged at 3200 RPM for 30 minutes, and cooled in a refrigerator for 2 hours. A small pellet of insoluble material was seen. The contents of two tubes was added equally to four Centriprep concentrators (Amicon Centriprep YM-30, 15 ml capacity tubes, Cat. No. 4307). These samples were centrifuged at 2000 RPM for 20 minutes, and the filtrates were removed and centrifuged again for 20 minutes. The contents of the remaining two tubes were added equally to same four Centriprep concentrators and centrifuged at 2000 RPM for 20 minutes. The filtrates were removed and centrifuged again for 20 minutes. The concentrates from the four Centriprep concentrators were combined into one of the Centriprep concentrators, with small washings, and centrifuged until the concentrate is ~2 ml.

The Sephadex column described in paragraph (A) was equilibrated with PE Storage Buffer. The PE concentrate was placed on the column and it was covered with aluminum foil to protect the column from light. The PE band was eluted and collected into a new Centriprep tube. The PE was concentrated to ~1 ml. The PE was transferred, with measurements of the volume, to a 15 ml disposable centrifuge tube covered with aluminum foil, with three small measured washings. The final PE concentrate has a known volume, calculated by adding the individual volumes (~2 ml).

A 20 µl sample was serially diluted to a final dilution of 800×, and read in a spectrophotometer using the PE program (at absorbances of $A_{280}$, $A_{565}$) and the PE concentration was calculated. The PE concentration multiplied by 800 yielded the PE concentration (the record concentration should be 70–95 mg/ml). The recovery was calculated by multiplying the concentration by the measured volume. The recovery was about 90%. This resulting PE concentrate was stored in a refrigerator.

C. Activation and Purification of Aminodextran

A 10 mg portion of purified, fractionated, desalted, freeze dried aminodextran MP8 (See Example 1) was weighed out and dissolved by vortex mixing with 1.00 ml phosphate buffered saline (PBS), in a 15 ml disposable centrifuge tube. Sulfosuccinimidyl 4-(N-maleimidomethyl) cyclohexane-1-carboxylate (sulfo-SMCC; Pierce, Prod. No. 22322) sample was weighed out (2.5 to 4.0 mg) and suspended in PBS (using 100 µl PBS per 1 mg SSMCC, a 10 mg/ml suspension) by vortex mixing. To the aminodextran solution was added 0.240 ml of sulfo-SMCC suspension and the reaction was roller mixed for 1.0 hour at room temperature (R.T.), resulting in an activated aminodextran solution.

The activated aminodextran solution was placed on a G-50 column (see paragraph A) connected to a Pharmacia Biotech UVICORD detector, 280 mn, time constant=2, range=1 AU and a Kipp & Zonen BD41 Chart Recorder, speed=1 mm/min, sensitivity=20 mV. After a void volume of about 12 ml, the recorder showed the aminodextran-SSMCC beginning to come off, and the product was collected into a 15 ml centrifuge tube, taking the peak to about one-half to two thirds down the trailing end, giving about 7 to 10 ml of purified aminodextran-SSMCC.

D. Activation and Purification of Streptavidin

The streptavidin (SA) was activated as follows: About 20 minutes after starting the aminodextran activation, a sample of streptavidin (Scripps Laboratories, San Diego, Calif.; Prod. No. S1214) was weighed out (2.0 to 3.0 mg), and transferred to a 15 ml disposable centrifuge tube. The SA was dissolved in PBS-EDTA, using 100 µl PBS-EDTA per 1 mg SA, giving a 10 mg/ml solution. A 2-iminothiolane hydrochloride (IT) (Sigma, Cat. No. I-6256) sample was weighed out (1.5 to3.0 mg) and dissolved in PBS-EDTA to give a 2 mg/ml solution. IT solution (0.0542 ml) per 1 mg SA was added to the streptavidin solution and this mixture was roller mixed for 1.0 hour at R.T.

The Streptavidin-IT was purified using the second G-50 column described in paragraph (A) and the above set-up, with sensitivity set to 500 mV. The Streptavidin-IT product was diluted with about 0.5 ml PBS-EDTA and placed on the column. After a void volume of about 14 ml, the product peak was seen on the chart recorder and the product was collected, giving about 5–6 ml. Briefly the SA-IT solution was vortexed and read on a Spectrophotometer, at $A_{280}$, using a 1 cm path cell and PBS-EDTA blank. The $A_{280}$ reading was divided by 3 to obtain the SA-IT concentration. The recovery of SA-IT was calculated and recorded as the concentration multiplied by the volume. The recovery was about 60 to 70%.

Based on the concentration of SA-IT calculated above, the volume of SA-IT solution needed to contain 1.00 mg SA-IT (1/conc. SA-IT) was calculated. This volume was added to the Aminodextran-SSMCC solution of paragraph (B) and roller mixed for two hours at R.T.

E. Activation and Purification of Phycoerythrin

Phycoerythrin was activated as follows: About 30 minutes after the start of the aminodextran-SSMCC–SA-IT reaction, the PE activation was started. The volume of PE concentrate needed to give 15 mg PE (15/PE concentration from above) was calculated and pipetted into an aluminum foil covered 15 ml centrifuge tube. The pipet tip was rinsed by drawing up 0.130 ml PBS-EDTA from a glass culture tube and adding it to the PE sample. (Because the PE concentrate was viscous and sticky, the tip was rinsed to reduce transfer loss). A 2-iminothiolane (IT) (Sigma, Cat. No. I-6256) sample was weighed out (1.5 to 3.0 mg) and dissolved in PBS-EDTA to give a 2 mg/ml solution. IT solution (0.0967 ml) was added to PE solution, and this mixture roller mixed for 1.0 hour at R.T.

PE-IT was purified as follows: Using the third G-50 column of paragraph (A), covered with aluminum foil, and above set-up, with sensitivity set to 1000 mV, the PE-IT was diluted with 0.5 ml PBS-EDTA and placed on the column. After a void volume of about 14 ml, the PE-IT peak was seen on the chart recorder and was collected into an aluminum foil covered 15 ml centrifuge tube, in a volume of 5–6 ml. After brief vortexing, a 20 ul sample was diluted into 980 µl PBS-EDTA (50× dilution). This sample was read on a spectrophotometer, using the PE program at $A_{280}$, $A_{565}$, which calculates the PE concentration. The concentration multiplied by 50 yields the PE-IT concentration. The recovery was calculated as the PE-IT concentration multiplied by the volume. The recovery was between 90–100%.

F. Conjugation Reaction of Aminodextran, Streptavidin and Phycoerythrin

The reaction of Aminodextran-SSMCC+SA-IT with PE-IT was formed by combining all of the PE-IT with the reaction mixture of Aminodextran-SSMCC+SA-IT. The mixture was roller mixed overnight at R.T.

After the conjugation, the following steps are employed to block any reactive groups. An L-cysteine (Sigma Cat. No. C-7755) solution was prepared at 5 mg/ml in PBS. A sample of L-cysteine (13–20 mg) was weighed out and dissolved in the calculated volume of PBS (Wt of L-Cys/5). The volume of L-cysteine solution to be added to the reaction mixture was calculated to be 0.120 times the volume of the reaction mixture (the reaction volume was calculated by summing the volumes of the components). L-cysteine was added and roller mixed for 30 minutes at R.T. An iodoacetamide (IA, Sigma Cat. No. I-6125) solution at 20 mg/ml in PBS was prepared. A sample of iodoacetamide (50–60 mg) was weighed and dissolved in the calculated volume of PBS (Wt of IA/20). The volume of IA solution to be added to the reaction mixture was calculated as 0.120 times the volume of the reaction mixture (the reaction volume from above plus the volume of L-cysteine solution). Iodoacetamide was added and the mixture roller mixed for 30 minutes at R.T.

G. Purification and Concentration of the SA-Aminodextran-PE Conjugate

Figure 6A:
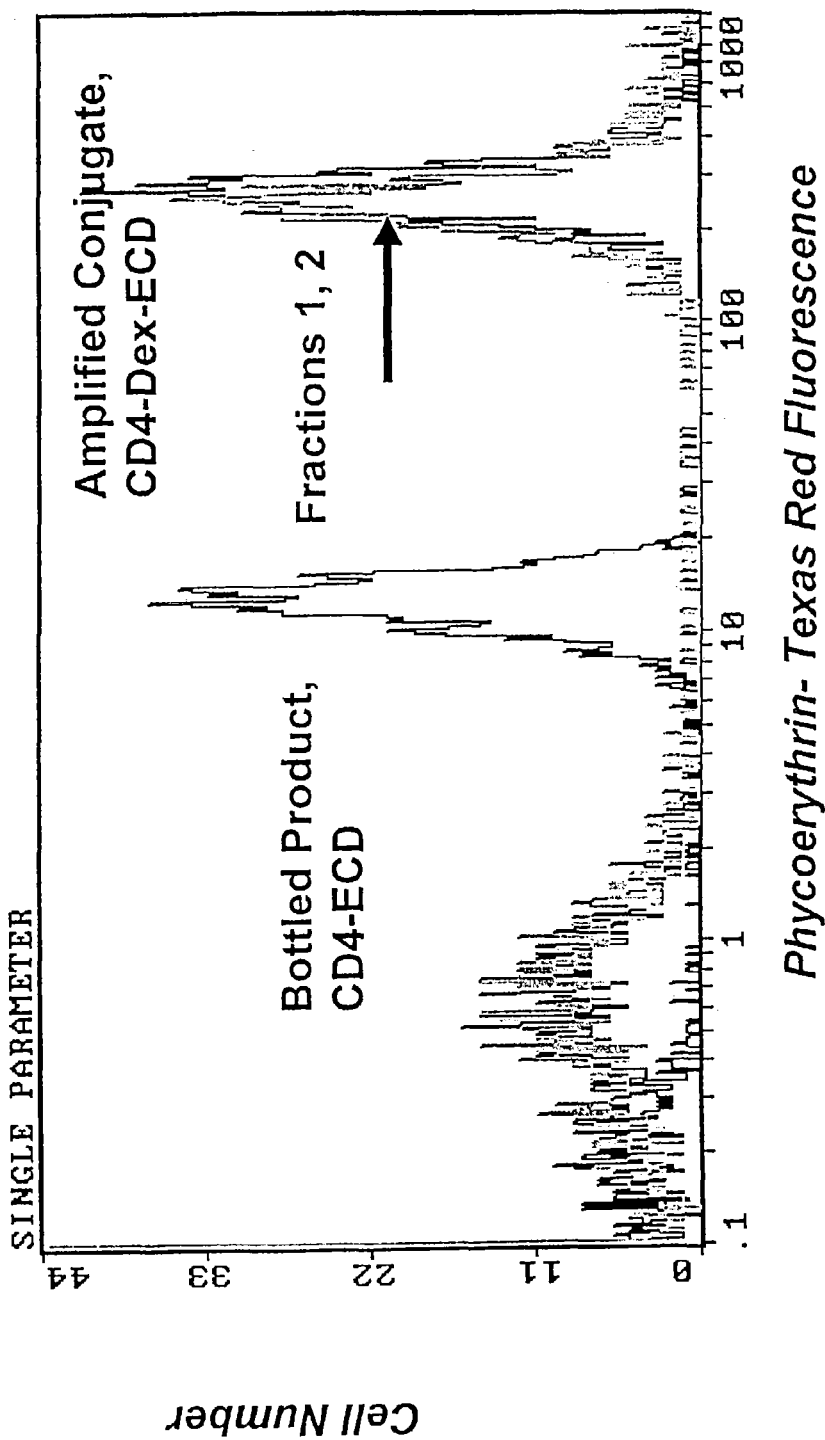
FIG. 6A is a flow cytometric histogram showing the labeling of lymphocytes as discussed in Example 6A below. This histogram shows the cell labeling results using as a direct label, an amplified antibody-aminodextran-phycobiliprotein conjugate (CD4-Dex-ECD) made with the improved polydisperse aminodextran of this invention compared to a labeled antibody directly conjugated to protein, i.e., no aminodextran, (CD4-ECD; available commercially from Beckman Coulter, Inc.). CD4-ECD is used as a control against which fluorescence intensities of the aminodextran crosslinked conjugate CD4-Dex-ECD is measured, when the conjugates are mixed with a cellular sample at or above saturation, i.e., when all antigenic sites targeted on the cell surface are occupied. This figure demonstrates that conjugates made with the improved Amdex of the invention provide significantly stronger fluorescence for the same cell number as does the control. The fractions are substantially identical.

The reaction mixture of paragraph F was placed into a Centriprep concentrator and concentrated to ~1.5–2.0 ml. The concentrate was placed on a Sepharose 4B column, 2.5 cm×46 cm, equilibrated and eluted with PBS or PBS-0.1 % NaN3. The column was connected to the detector and chart recorder as specified above, and the output was connected to a fraction collector (Pharmacia LKB-FRAC-100, with drop counter). The fraction collector was loaded with 12×75 glass culture tubes and was programmed to collect 120 drops (~3.8 ml) per tube. The flow rate was approximately 2.75–3.50 minutes/tube. The column was wrapped in aluminum foil. The chart recorder sensitivity was set to 50 mV. The conjugate began to elute at fraction 17, and continued to fraction 24, which corresponds to a large conjugate peak. The column was allowed to run until the small molecules had eluted, which was by fraction 62. The resulting small peaks corresponded to unreacted PE and SA, and a final peak contained low molecular weight material. The main product band was off-scale at this sensitivity, but the free PE and streptavidin bands were on-scale. A sample chromatogram is shown in FIG. 6A for one run and compared to another run FIG. 6B in which non-purified amino dextran, MP8, was used. The product fractions (usually 17–23) were labeled and protected from light. These conjugate fractions were briefly vortexed and measured in the spectrophotometer at $A_{280}$ and $A_{565}$ nm, using the PE program described below. The fractions were not diluted, and were read in a 1 mm path cell. Calculations are based on these measurements (see below). After reading, each sample was put back into its tube. The tubes were stoppered and stored in a refrigerator H. Analysis of Conjugate Fractions A spectrophotometer gives $A_{280}$, $A_{565}$, $A_{280}/A_{565}$, $A_{565}/A_{280}$, Protein Concentration (calculated from the $A_{280}$ corrected for PE), and PE Concentration. The Protein and PE concentration values are multiplied by ten because the readings were in a 1 mm path cell. The PE Concentration Values are summed to give the total PE concentration. This value is multiplied by the fraction volume (3.8 ml) to give the total recovered PE (in mg). The total recovered PE divided by the amount of PE-IT recovered and used in the conjugation reaction gives the "yield" based on PE (typically 70–75%). The amount of aminodextran used for the conjugation (10 mg) is divided by its molecular weight (determined by triple detector method—$2.734 \times 10^6$ g/m) to give the molar aminodextran amount (3.6576 nmol). The amount of total recovered PE divided by 240,000 gives the molar amount of PE in the conjugate (i.e., ~10.5 mg=44 nmol). The ratio of PE nmol/aminodextran nmol gives the approximate number of PE molecules per aminodextran molecule (i.e., ~11).

The Protein concentration values (multiplied by ten) for each fraction divided by three (i.e., the absorbance factor for streptavidin) provides the "monoclonal antibody (MCA) equivalent concentration". The MCA equivalent concentration is used as a guide in determining the dose of reagent to be used for staining cells for flow analysis.

Spectrophotometer formulas used for calculations are as follows:

PE Conc.=$A_{565} \times 0.12244$

Protein Conc.=$A_{280}-(A_{565} \times 0.1714)$

I. Process Condition Selections

It was known from experiments with aminodextran conjugates of monoclonal antibody and Phycoerythrin (PE) that a relatively small amount of antibody is needed and the remainder of the aminodextran binding sites should be occupied with PE to get the best amplifications (theoretically one antibody per aminodextran chain is required). It was found in other work with p24 conjugates that streptavidin needs to be used at somewhat higher levels compared to antibody, perhaps because SA does not react well, or is partially inhibited upon binding to aminodextran. It was found that it was better to react sulfoSMCC-activated aminodextran (better than activation with 2-iminothiolane which can result in disulfide crosslinking) first with a relatively small amount of 2-iminothiolane-activated SA (SA has no disulfide bonds and must be activated with 2-iminothiolane rather than the DTT method preferred for monoclonal antibodies), followed by an excess of 2-iminothiolane-activated PE.

Comparison of 10 minute wait to a 2 hour wait between SA-IT and PE-IT additions, gave similar but better results with two hour wait. Comparison of 0.5 mg, 1.0 mg, and 2.0 mg of SA-IT gave best results using 1.0 mg SA-IT. PE-IT is always used at 13–15 mg, which gives near saturation of the 10 mg sulfoSMCC-aminodextran, with only a small amount of unreacted PE left.

Example 5

Preparation of
Antibody-Aminodextran-Phycobiliprotein
Conjugates

A. Materials

Unless otherwise identified, materials mentioned in Example 4 are provided by the same sources.

Phosphate-buffered saline, 1×PBS, pH 7.1–7.3, and conductivity 13,500–15,500 µmho-cm$^{-1}$, was prepared by dilution with distilled water from a 20×PBS stock solution, which contains 26.9 g dm$^{-3}$ of $K_2HPO_4$, 6.4 g dm$^{-3}$ of $KH_2PO_4$, and 170.0 g dm$^{-3}$ of NaCl.

The CD4 antibody (CD4 clone SFCI12T4D11 (IgG1)) and CD8β antibody (CD8β clone 2ST8.5H7(IgG2a)), CD8β-PC5, anti-CD4-PE and anti CD4-ECD are products of Beckman Coulter Cell Analysis Division, Miami, Fla.

B. Preparation of Antibody-Aminodextran-Phycobiliprotein Conjugates

The procedure was similar to the described in U.S. Pat. No. 5,791,741, incorporated by reference herein, to prepare antibody-Aminodextran-PE conjugates. Herein, an iminothiolane-activated streptavidin or dithiothreitol(DTT) (Sigma)-activated monoclonal antibody and, then, an iminothiolane-activated fluorescent protein, PE, PC5, or ECD, were conjugated stepwise to the sulfo-SMCC-activated aminodextran. The IT to SA, DTT to MCA, and IT to PE (PC5, ECD) molar ratios were maximized at 15, 50, and 22.5, respectively, so as not to interfere with SA or MCA activity, or with PE (PC5, ECD) fluorescence intensity.

C. CD8β Antibody-Aminodextran-PC5 Conjugate

Conjugation was carried out with molar ratio of 43:4.3:1=PC5:CD8β antibody:purified aminodextran-MP8 of Example 1. The weight ratio was 12.856: 0.858:10 at a 10 mg aminodextran scale.

Aminodextran was activated with sulfo-SMCC as follows: 1.58 mL of a 6.63 mg/mL solution of Aminodextran in 1×PBS were activated with 0.180 mL of 10 mg/mL sulfo-SMCC solution in 1×PBS. The mixture was roller mixed for about one hour at room temperature. After the mixing was completed, the reaction mixture was immediately applied to the top of a 60 mL (1.7 cm×28 cm) G-50 Sephadex column equilibrated with 1×PBS. The sample was eluted using 1×PBS and collected in about 2 mL fractions. Fractions of the first band absorbing at 280 nm contained the high molecular weight activated aminodextran as was verified by Tyndall scatter with a focused visible light beam (Model 650, Cambridge Instruments, Inc., Buffalo, N.Y.). These fractions were pooled to give about 3.3 mL total sulfo-SMCC-activated aminodextran.

CD8β monoclonal antibody was activated by the addition of 0.048 mL of a 5 mg/mL solution of DTT in 1×PBS, 2 mM EDTA and 0.871 mL 1×PBS, 2 mM EDTA to 0.081 mL of CD8β concentrate (61.67 mg/mL). The resulting solution, which had an antibody concentration of 5 mg/mL and a DTT molar concentration fifty-fold larger, was mixed at ambient temperature for about one hour. The reaction mixture was then chromatographed on a 60 mL (1.7 cm×28 cm) G-50 Sephadex column equilibrated with 1×PBS, 2 mM EDTA and the sample was eluted using 1×PBS, 2 mM EDTA. The first band peak fraction yielded about 1.0 mL of 3.722 mg/mL antibody solution, which contained a total of 3.72 mg DTT-activated CD8β antibody derivative.

Conjugation of DTT- CD8β to sulfo-SMCC-aminodextran occurred by reacting 0.858 mg MCA, a 10 mg aminodextran weight ratio, and adding 0.231 mL of 3.72 mg/mL DTT-CD8β solution were added into a 3.3 mL of sulfo-SMCC-aminodextran solution. The mixture was roller mixed for 2 hours.

PC5 was activated by the addition of 0.116 mL of a 2 mg/mL solution of iminothiolane in 1×PBS and 0.032 mL 1×PBS to 0.302 mL of PC5 concentrate (59.7 mg/mL). The resulting solution, which had a PC5 concentration of 40 mg/mL and an iminothiolane molar concentration 22.5-fold larger, was mixed at room temperature for about one hour. The reaction mixture was then applied to the top of a 60 mL (1.7 cm×28 cm) G-50 Sephadex column equilibrated with 1×PBS and the sample was eluted with 1×PBS. The first band peak fraction gave about 4.14 mL of 4.005 mg/mL PC5 at an $A_{565}/A_{280}$ ratio of 5.623, which contained a total of 16.581 mg IT-PC5.

Conjugation of IT-PC5 to the DTT- CD8β+sulfo-SMCC-aminodextran reaction mixture occurred as follows: After mixing DTT- CD8β and sulfo-SMCC-Aminodextran for 2 hours, 3.210 mL of 4.005 mg/mL IT-PC5 representing 12.856 mg IT-PC5 was added to the mixture, which was roller mixed overnight for 16–24 hours. After the mixing was completed, the total volume of the mixture was determined and 0.120 times this volume of 5 mg/mL L-cysteine in 1×PBS was added to the conjugation mixture. The L-cysteine containing mixtures were then mixed for an additional 15 minutes to effect blocking of any unreacted sulfo-SMCC moieties. Lastly, 20 mg/mL iodoacetamide in 1×PBS in the amount of 0.120 times the total mixture volume and 1M borate buffer solution, pH 9.8, in the amount of 0.020 times the total mixture volume were added to each mixture. The resulting mixtures were mixed for about 30 minutes to block any unreacted sulfhydryl groups.

Purification of CD8β-Aminodextran-PC5 conjugate was accomplished as follows: The total volume of conjugation mixture was reduced to about 2.0 mL by centrifuging an Amicon Centri-Prep 30 tube containing the sample for about 30 minutes at 2000 rpm using an IEC Centra-8 centrifuge. The sample was placed on the top of a Bio-Gel A-15 m agarose column (BioRad Laboratories, Inc., 2.5 cm×48 cm) equilibrated with 1×PBS and chromatographed using 1×PBS as eluant. Eluant fractions of about 3.6 mL volume were collected using a Pharmacia LKB FRAC-100 collector operating in the drop collection mode. The fractions were monitored using a LKB 2138 Uvicord S monitor operating at 280 nm.

The first well-separated, narrow, intense band eluted from the column in fractions #19 to #23 contained the CD8β-aminodextran-PC5 conjugate. The broad hump usually overlapping and following this narrow first band was absent due to the removal of almost all of the low molecular weight contaminant of aminodextran, which had a broad size distribution. A second intense band peaking at about fraction #47 contained excess PC5, and a medium-to-low intensity well-separated third band peaking at about fraction #62 was attributed to the low molecular weight excess blocking reagents. The fractions collected for the CD8β-Aminodextran-PC5 conjugate were analyzed spectrophotometrically at wavelengths of 565.5 and 280 nm using a 1 mm path length cell. The concentration of PC5 in mg/mL in the conjugate was derived from the absorbance at 565.5 nm by using the formula, $A_{565.5}/8.167$. Data for fractions 19 to 23 under the first narrow peak gave 6.264 mg total PC5 in the conjugate. Since 12.856 mg IT-PC5 was used in conjugation, the yield was 48.7%.

D. CD4 Antibody-Aminodextran-ECD Conjugate

The procedures were similar to those outlined for the preparation of the anti-CD8β-Aminodextran-PC5 conjugate, except anti-CD4 antibody was activated with DTT and used in the conjugation instead of CD8β antibody, and the tandem PE-Texas red or ECD fluorescent dye was used instead of PC5. In trial 2, DTT-CD4 (0.858 mg) was mixed with sulfo-SMCC-Aminodextran (10 mg) at concentrations of 0.141 and 1.647 mg/mL, respectively, during the first 2 hour step in conjugation. Then, 5.102 mL of IT-ECD (12.856 mg) were added to the mixture, which was further roller mixed overnight for 16–24 hours. The IT-ECD ($A_{565.5}/A_{280}$) ratio was 4.968. The conjugation mixture was concentrated to about 1.0 mL and applied to the top of a Sepharose 4B column. Data for fractions 19–23, collected at about 3.6 mL per fraction under the first narrow peak in trial 2, gave 6.098 mg total ECD in the conjugate. Since 12.856 mg IT-ECD was used in conjugation, the yield was 47.4%.

Figure 6B:
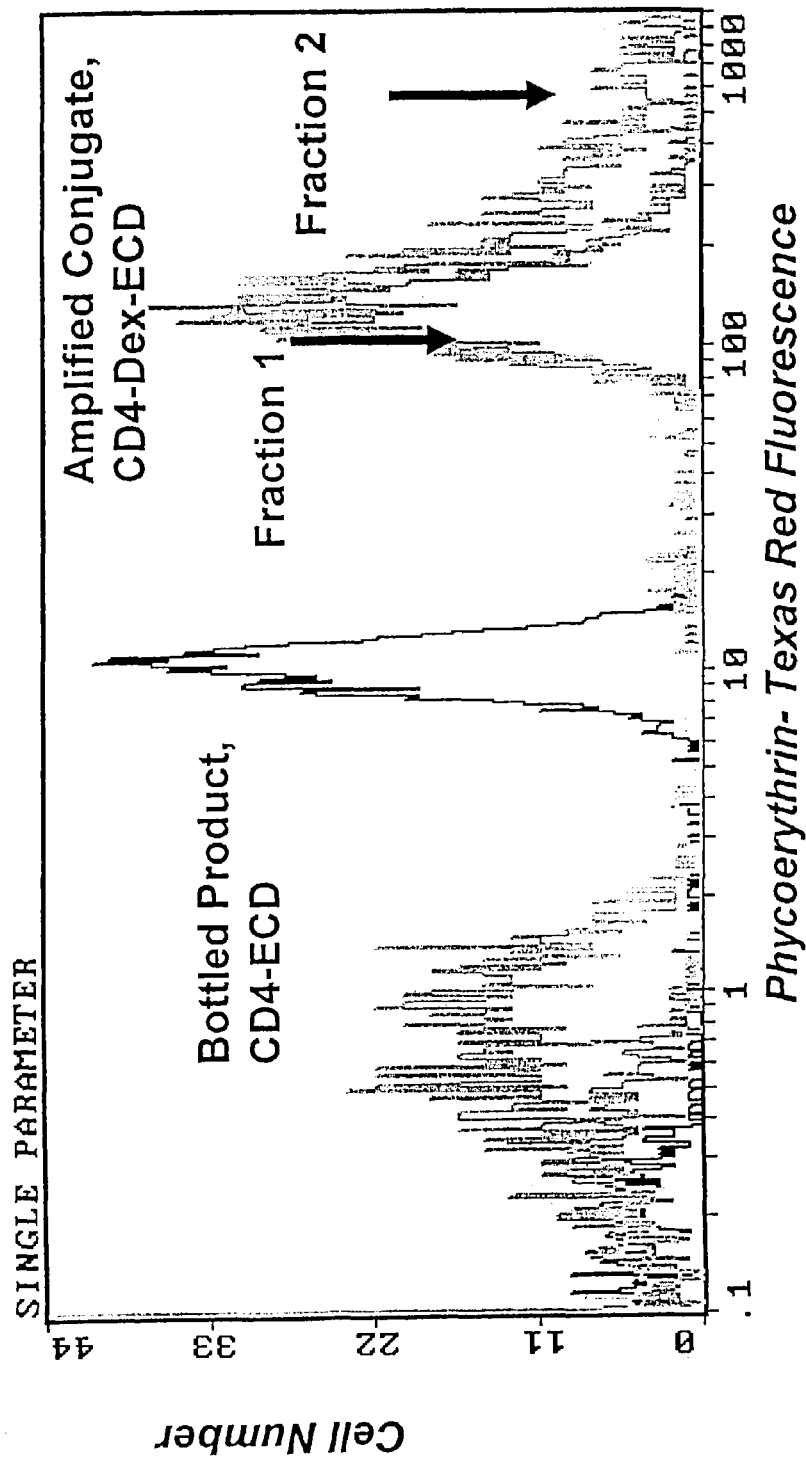
FIG. 6B is a similar histogram showing the cell labeling results using as a direct label, an amplified antibody-aminodextran-phycobiliprotein conjugate (CD4-Dex-ECD) made with standard aminodextran. Histograms of two fractions of the product are shown. In comparison with FIG. 6A, the two fractions vary due to the non-homologous aminodextran in the conjugate.

An example of the effect of aminodextran-MP8 purification on the chromatograms of CD4 antibody-aminodextran-PE conjugates applied to a Sepharose 4B column, 2.5 cm×46 cm, equilibrated and eluted with 1×PBS is shown in FIG. 6B.

In the above experiments, because of the very large amounts of phycobiliprotein in the conjugates, the usual calculation of antibody concentration from absorbance measurements at 280 and 565 nm could not be reliably performed. However, the concentration of reacting (conjugate) units of antibody-Aminodextran-PE was obtained by dividing the PE concentration, determined from the absorbance at 565 nm, by the normalized molar ratio of PE to Aminodextran. First, the mol PE was calculated by summing the concentration of PE in the fractions under the first narrow conjugate band, and multiplying by the volume per fraction, and dividing by the MW of PE. Second, all of the aminodextran was assumed to react and be retained in the first band. The mol Aminodextran was calculated by dividing the mass of Aminodextran used by the MW of 8.0 MDa determined.

Example 6

Flow Cytometric Analyses Using Improved Amdex

A. Use of the Conjugates of Example 5

CD8β-PC5 (commercially available as Item 6607109, in the 2003 Beckman Coulter, Inc., Cell Analysis Catalog) and fractions of CD8β-Aminodextran-MP8, both standard MP8 and improved (or prepurified) MP-8, -PC5 conjugates were titered with 2.5, 1.25, and 0.625 μg of antibody in the conjugate per tube. Amounts of antibody for the titers were determined from corrected $A_{280}$ values for the direct conjugate, and by an indirect method described below for the aminodextran-crosslinked conjugates. Dilutions were added to 100 μL of whole blood and incubated for 10 minutes at room temperature.

For analysis on a flow cytometer (COULTER® EPICS® 4-color XL-MCL™), the blood mixtures were: lysed and quenched using the COULTER™ ImmunoPrep™ reagent system on the COULTER™ Q-Prep™ workstation, washed once with 1×PBS (addition of 2 mL of 1×PBS, centrifugation at 500 g for 5 min, discarding supernatant), and the cell pellet was resuspended in 1 mL of 1×PBS. The lymphocyte cell population was distinguished with forward light scatter vs. 90° C. light scatter, electronically gated, and displayed on single parameter histograms (y-axis=number of fluorescent events (count); x-axis=fluorescence intensity). Flow cytometer instrument settings were adjusted to display the non-staining negative lymphocyte sub-population only within the $1^{st}$ decade on the 4-decade log scale for fluorescence intensity.

Figure 10:
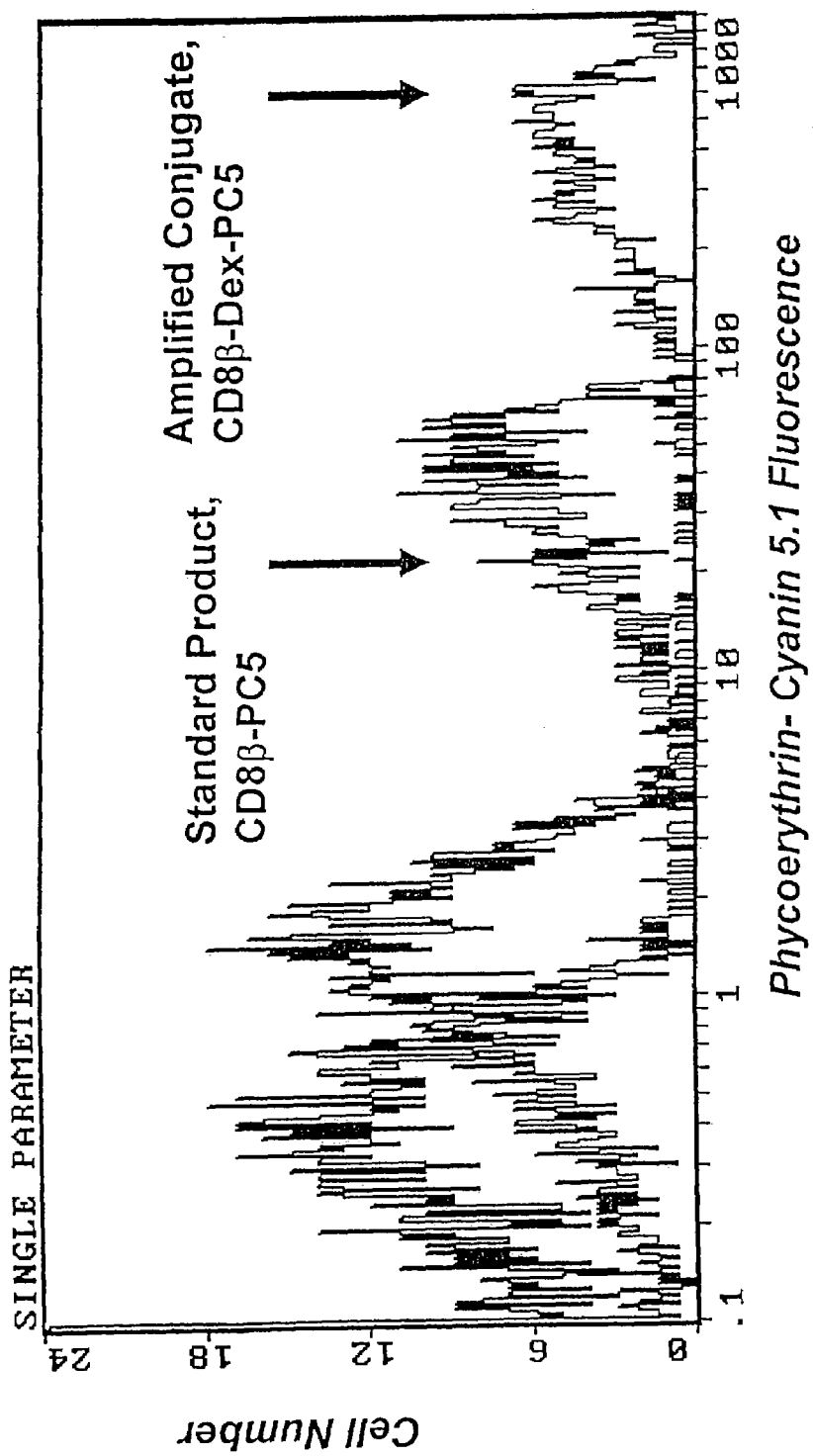
FIG. 10 shows overlayed histograms comparing the direct amplified conjugate CD8β-Dex-PC5 made with the improved aminodextran of the invention to the control CD8β-PC5, comparing cell number to fluorescence. These data demonstrate the significant improvement in fluorescent intensity using the amplified improved reagent as opposed to standard bottled product.

FIG. 10 shows the ability of CD8β-Aminodextran-PC5 conjugate as a fluorescent marker containing more than two PC5 molecules per dextran molecule, to enhance the mean channel PC5 fluorescence intensity (MFI) of the positive cell population over that obtained with the direct CD8β-PC5 conjugate which contains only 1 PC5 per antibody and no aminodextran. This is the control against which fluorescence amplification is measured. Again, the data demonstrate the significant improvement in fluorescent intensity using the amplified CD8β reagent as opposed to standard bottled product.

Figure 7A:
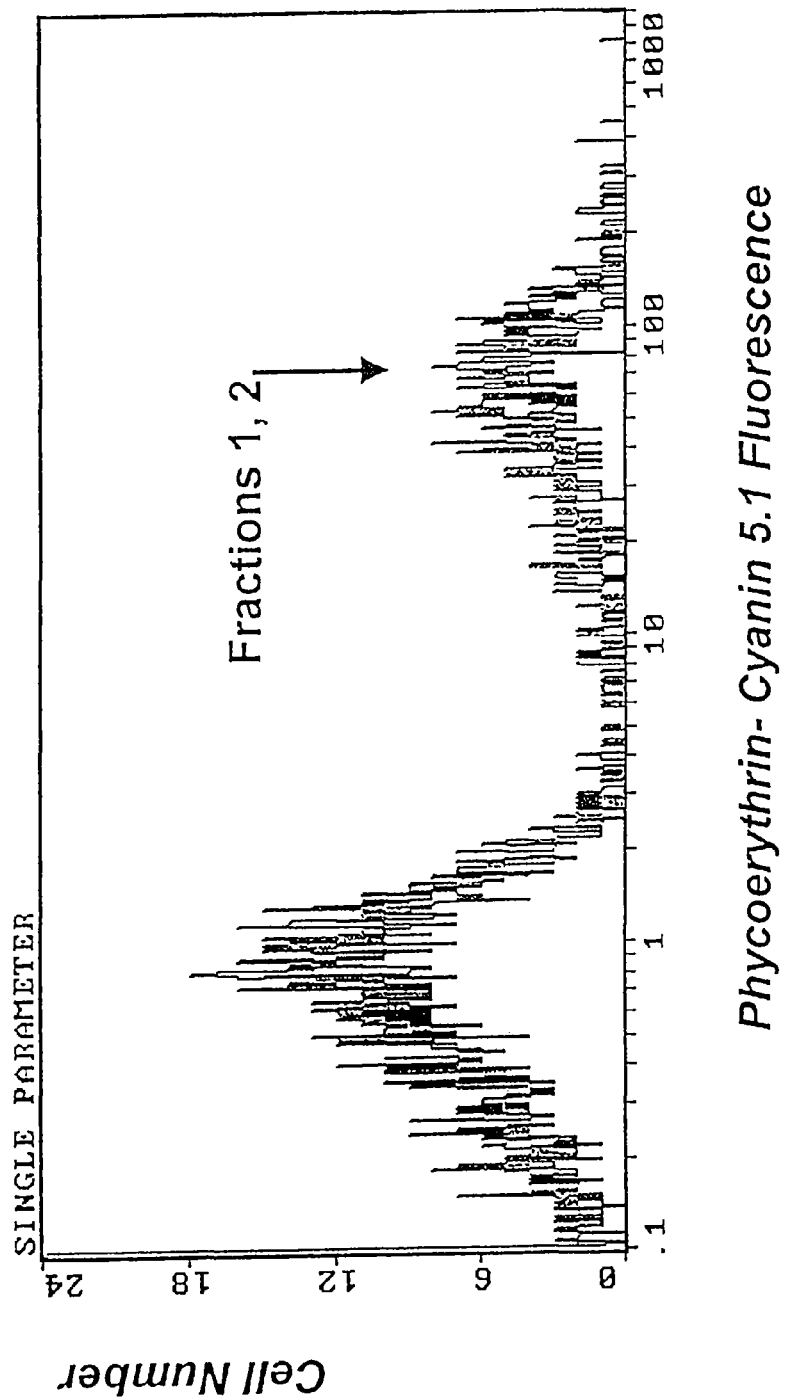
FIG. 7A is a flow cytometric histogram showing the labeling of lymphocytes as discussed in Example 6A below. This histogram shows the cell labeling results using as a direct label, an amplified antibody-aminodextran-phycobiliprotein conjugate (CD8β-Dex-PC5) made with the improved aminodextran of this invention.
Figure 7B:
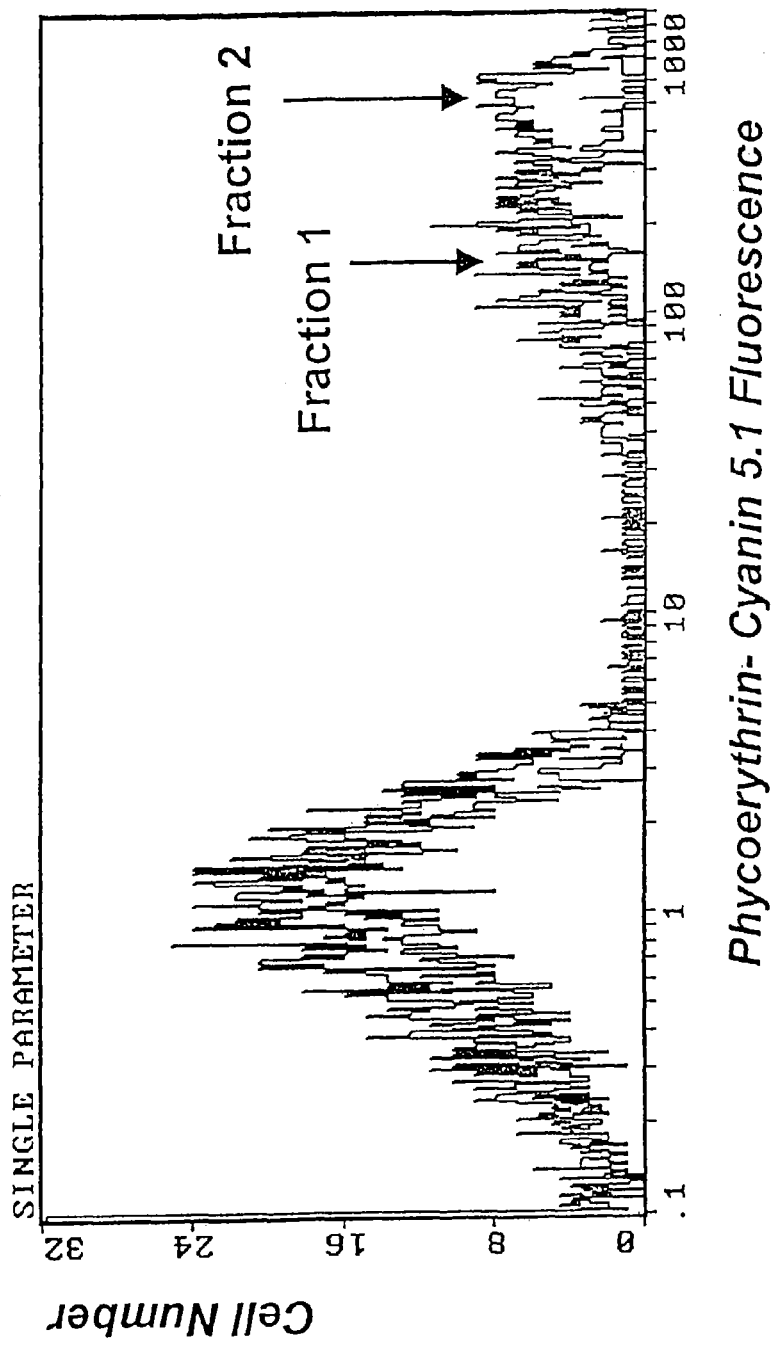
FIG. 7B is a flow cytometric histogram showing the labeling of lymphocytes as discussed in Example 5A below. This histogram shows the cell labeling results using as a direct label, an amplified antibody-aminodextran-phycobiliprotein conjugate (CD8β-Dex-PC5) made with conventional heterogeneous aminodextran of the prior art.

FIGS. 7A and 7B are histograms showing that the crosslinked conjugates with standard Aminodextran-MP8 and purified Aminodextran-MP8 have up to 3.5- and 10-fold, respectively, higher fluorescence intensity on CD8β+lymphocytes. Titers of the control, CD8β-PC5, and the samples, CD8β-Aminodextran-MP8 (standard and purified)-PC5, with the same instrument settings were run and the results, mean channel PC5 fluorescence intensities and MFI ratios, sample fraction-to-control at same titers, are presented in Tables 3 and 4.

TABLE 3

CD8β-purified AMDEX-PC5

| Microgram/test | Control 1 | Fraction 19 | Fraction 20 | Fraction 21 |
|---|---|---|---|---|
| Mean Channel PC5 Fluorescence Intensities (MFI) | | | | |
| 2.5 | | 480.8 | 362.3 | |
| 1.25 | 41.4 | 415.7 | 458.4 | 255.4 |
| 0.625 | | 313.5 | 372.2 | 438.5 |
| MFI Ratios, Fraction/Control 1 | | | | |
| 2.5 | | 12 | 9 | |
| 1.25 | 1.0 | 10 | 11 | 6 |
| 0.625 | | 8 | 9 | 11 |
| Percent Positive, CD8β Lymphocytes | | | | |
| 2.5 | | 21.1 | 12.9 | |
| 1.25 | 25.6 | 10.1 | 16.7 | 19.4 |
| 0.625 | | 6.37 | 9.47 | 17.2 |

TABLE 4

CD8β-standard AMDEX-PC5

| Microgram/test | Control 1 | Fraction 19 | Fraction 20 | Fraction 21 | Fraction 22 |
|---|---|---|---|---|---|
| Mean Channel PC5 Fluorescence Intensities (MFI) | | | | | |
| 2.5 | | 88 | 67 | | |
| 1.25 | 24 | 88 | 62 | 41 | 31 |
| 0.625 | | 76 | 60 | 34 | |

TABLE 4-continued

CD8β-standard AMDEX-PC5

| Microgram/test | Control 1 | Fraction 19 | Fraction 20 | Fraction 21 | Fraction 22 |
|---|---|---|---|---|---|
| MFI Ratios, Fraction/Control 1 | | | | | |
| 2.5 | | 4 | 3 | | |
| 1.25 | 1.0 | 4 | 3 | 2 | 1 |
| 0.625 | | 3 | 3 | 1 | |
| Percent Positive, CD8β Lymphocytes | | | | | |
| 2.5 | | 19 | 19 | | |
| 1.25 | 20 | 18 | 18 | 18 | 19 |
| 0.625 | | 18.5 | 17 | 19 | |

CD4-ECD and fractions of CD4-Aminodextran-MP8 (standard and purified)-ECD conjugates were titered with 2.5, 1.25, and 0.625 μg per tube in the same way as in the previous description. The results are shown in FIGS. 6A and 6B for the positive population mean channel ECD fluorescence intensities (MFI) for the CD4+ lymphocytes with the direct and crosslinked antibody-ECD conjugates. The MFI ratios, maximizing at 20.8 and 27.2 were calculated from the mean channel positions of each Aminodextran sample compared to the saturating bottle product dose of CD4-ECD (0.5 μg), as displayed in Tables 5 and 6.

TABLE 5

CD4-purified AMDEX-ECD

| Microgram/test | Control 1 | Fraction 18 | Fraction 19 | Fraction 20 | Fraction 21 |
|---|---|---|---|---|---|
| Mean Channel ECD Fluorescence Intensities (MFI) | | | | | |
| 2.5 | | | 282 | 329 | |
| 1.25 | 12.1 | 200 | 270 | 293 | 248 |
| 0.625 | | | 276 | 267 | |
| MFI Ratios, Fraction/Control 1 | | | | | |
| 2.5 | | | 23 | 27 | |
| 1.25 | 1.0 | 16.5 | 22 | 24 | 20 |
| 0.625 | | | 23 | 22 | |
| Percent Positive, CD4 Lymphocytes | | | | | |
| 2.5 | | | 45 | 45 | |
| 1.25 | 45.5 | 40.6 | 42 | 45 | 41 |
| 0.625 | | | 44 | 43 | |

TABLE 6

CD4-standard AMDEX-ECD

| Microgram/test | Control 1 | Fraction 18 | Fraction 19 | Fraction 20 | Fraction 21 |
|---|---|---|---|---|---|
| Mean Channel ECD Fluorescence Intensities (MFI) | | | | | |
| 2.5 | | 146 | 215 | 152 | |
| 1.25 | 10.3 | 120 | 170 | 132 | 108 |
| 0.625 | | 99 | 133 | 111 | 102 |
| MFI Ratios, Fraction/Control 1 | | | | | |
| 2.5 | | 14 | 21 | 15 | |
| 1.25 | 1.0 | 12 | 17 | 13 | 11 |
| 0.625 | | 10 | 13 | 11 | 10 |
| Percent Positive, CD4 Lymphocytes | | | | | |
| 2.5 | | 37 | 37 | 41 | |
| 1.25 | 40.8 | 36 | 37 | 41 | 42 |
| 0.625 | | 39 | 39 | 40 | 42 |

The data in Tables 3–6 demonstrate that for both the CD4 and Streptavidin conjugates, at all doses tested for the fractions, the standard deviation (variation) was significantly higher for the standard aminodextran compared to the fractionated, purified aminodextran of this invention, indicating for both fractionated purified aminodextran conjugates, a more homogeneous product with a correspondingly greater yield. For the CD8β conjugates, the results were essentially equivalent comparing fractionated, purified aminodextran to standard aminodextran.

B. Use of the Conjugates of Example 4

Several trials were conducted using streptavidin-Aminodextran-MP8 (standard and purified)-PE conjugates to label lymphocytes. The lymphocytes were bound primarily to CD4-biotin and then washed. The conjugates were used as indirect secondary reagents with the biotinylated CD4 primary antibody to label and analyze for CD4+ cells in whole blood by flow cytometry. Specifically, titers of 0.625, 1.25, and 2.5 μg of streptavidin-PE control conjugate and aminodextran-crosslinked conjugates with 100 μL of whole blood (previously stained with biotinylated CD4 antibody and washed once), were lysed, quenched, washed, and analyzed.

The fluorescence intensity was compared to lymphocytes from the same donor 1) directly marked with CD4-PE (available commercially as Item 6603850 from the 2003 Beckman Coulter Inc. Cell Analysis catalog) and with 2) indirectly marked CD4-biotin and bottle product SA-PE. Usually two different donors were used.

Figure 8A:
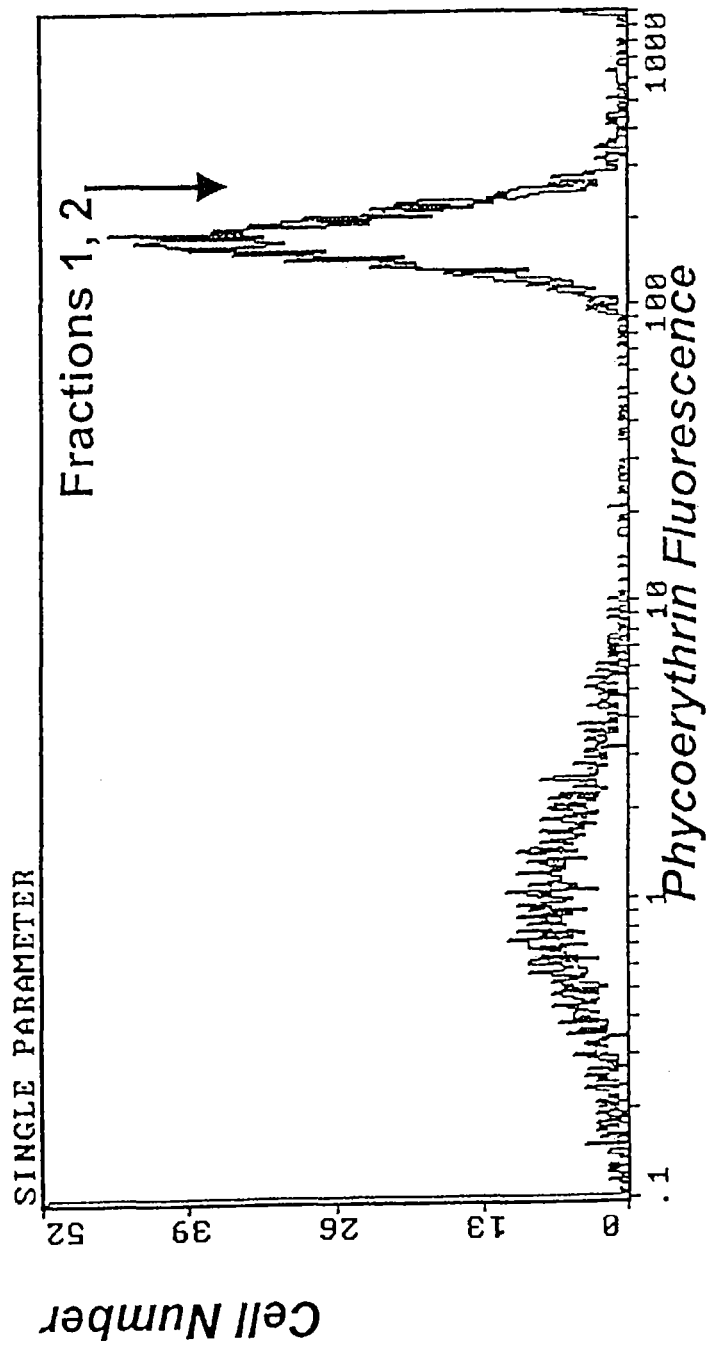
FIG. 8A is a flow cytometric histogram showing the labeling of lymphocytes as discussed in Example 6B below. This histogram shows the cell labeling results using as a direct label, biotinylated CD4 (CD4-Biotin) and as an indirect or secondary label, an amplified streptavidin-aminodextran-phycobiliprotein conjugate (SA-Dex-PE) made with the improved aminodextran of this invention. This data show that different fractions obtained using improved aminodextran are virtually identical.
Figure 8B:
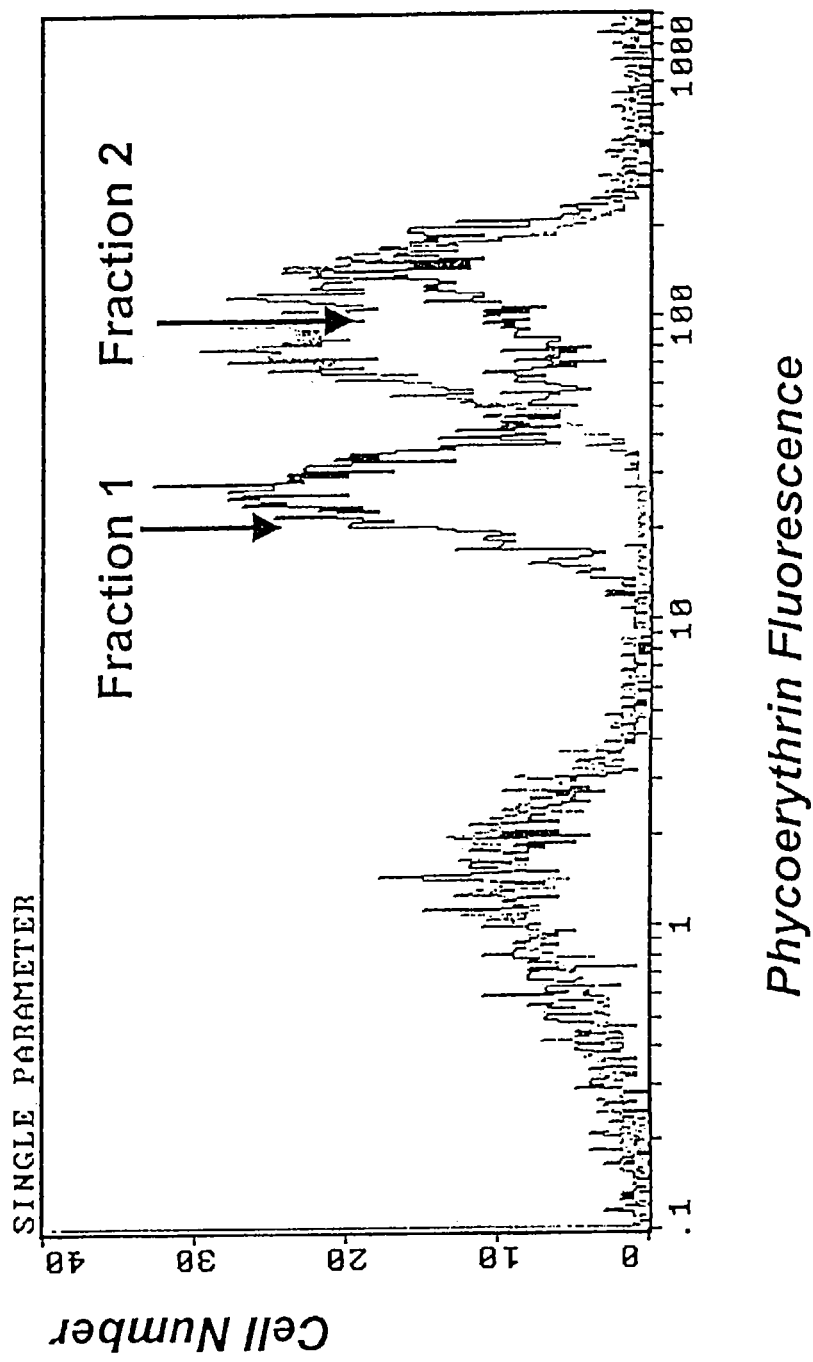
FIG. 8B is a flow cytometric histogram showing the labeling of lymphocytes as discussed in Example 6B below. This histogram shows the cell labeling results using as a direct label, biotinylated CD4 (CD4-Biotin) and as an indirect or secondary label, an amplified streptavidin-aminodextran-phycobiliprotein conjugate (SA-Dex-PE) made with conventional heterogeneous aminodextran of the prior art. In contrast with FIG. 8A, these data show clear differences between the two fractions obtained using the standard method. Moreover, the two peaks seen in fraction 1 of FIG. 8B would give rise to some questions concerning specificity, possibly raising concern about the overall accuracy of that fraction to measure the quantity of antigen.

The results are shown in the overlaid histograms of FIGS. 8A and 8B. The conjugates prepared from purified aminodextran fractions of the present invention generally had 10–15 fold higher fluorescence, when compared to directly labeled cells, and ~4 fold higher fluorescence when compared to indirectly labeled cells. See, also Tables 7 and 8.

TABLE 7

Streptavidin-purified AMDEX-PE

| Microgram/test | Control 1 | Control 2 | Fraction 18 | Fraction 19 | Fraction 20 | Fraction 21 |
|---|---|---|---|---|---|---|
| Mean Channel PE Fluorescence Intensities (MFI) | | | | | | |
| 2.5 | | | 185.9 | 192.6 | 182.5 | 178.7 |
| 1.25 | 16.0 | 43.9 | 156.4 | 149.1 | 165.8 | 147.0 |
| 0.625 | | | 112.4 | 72.5 | 121.3 | 115.1 |
| MFI Ratios, Fraction/Control 1 | | | | | | |
| 2.5 | | | 11.6 | 12.0 | 11.4 | 11.2 |
| 1.25 | 1.0 | 2.7 | 9.8 | 9.3 | 10.4 | 9.2 |
| 0.625 | | | 7.0 | 4.5 | 7.6 | 7.2 |
| Percent Positive, CD4 Lymphocytes | | | | | | |
| 2.5 | | | 44.0 | 49.1 | 52.0 | 47.8 |
| 1.25 | 50.4 | 51.4 | 46.3 | 46.1 | 47.5 | 46.1 |
| 0.625 | | | 47.4 | 47.2 | 44.6 | 47.9 |

TABLE 8

Streptavidin-standard AMDEX-PE

| Microgram/test | Control 1 | Control 2 | Fraction 18 | Fraction 19 | Fraction 20 | Fraction 21 |
|---|---|---|---|---|---|---|
| Mean Channel PE Fluorescence Intensities (MFI) | | | | | | |
| 2.5 | | | 9.7 | 97.7 | 86.2 | 126.0 |
| 1.25 | 24.0 | 84.0 | 23.9 | 66.6 | 82.3 | 83.3 |
| 0.625 | | | 34.3 | 39.0 | 97.4 | 84.3 |
| MFI Ratios, Fraction/Control 1 | | | | | | |
| 2.5 | | | 0.4 | 4.1 | 3.6 | 5.3 |
| 1.25 | 1.0 | 3.5 | 1.0 | 2.8 | 3.4 | 3.5 |
| 0.625 | | | 1.4 | 1.6 | 4.1 | 3.5 |
| Percent Positive, CD4 Lymphocytes | | | | | | |
| 2.5 | | | 24.7 | 59.3 | 56.8 | 55.1 |
| 1.25 | 58.3 | 57.1 | 20.4 | 24.8 | 9.9 | 20.3 |
| 0.625 | | | 13.6 | 16.5 | 21.7 | 11.0 |

Figure 9:
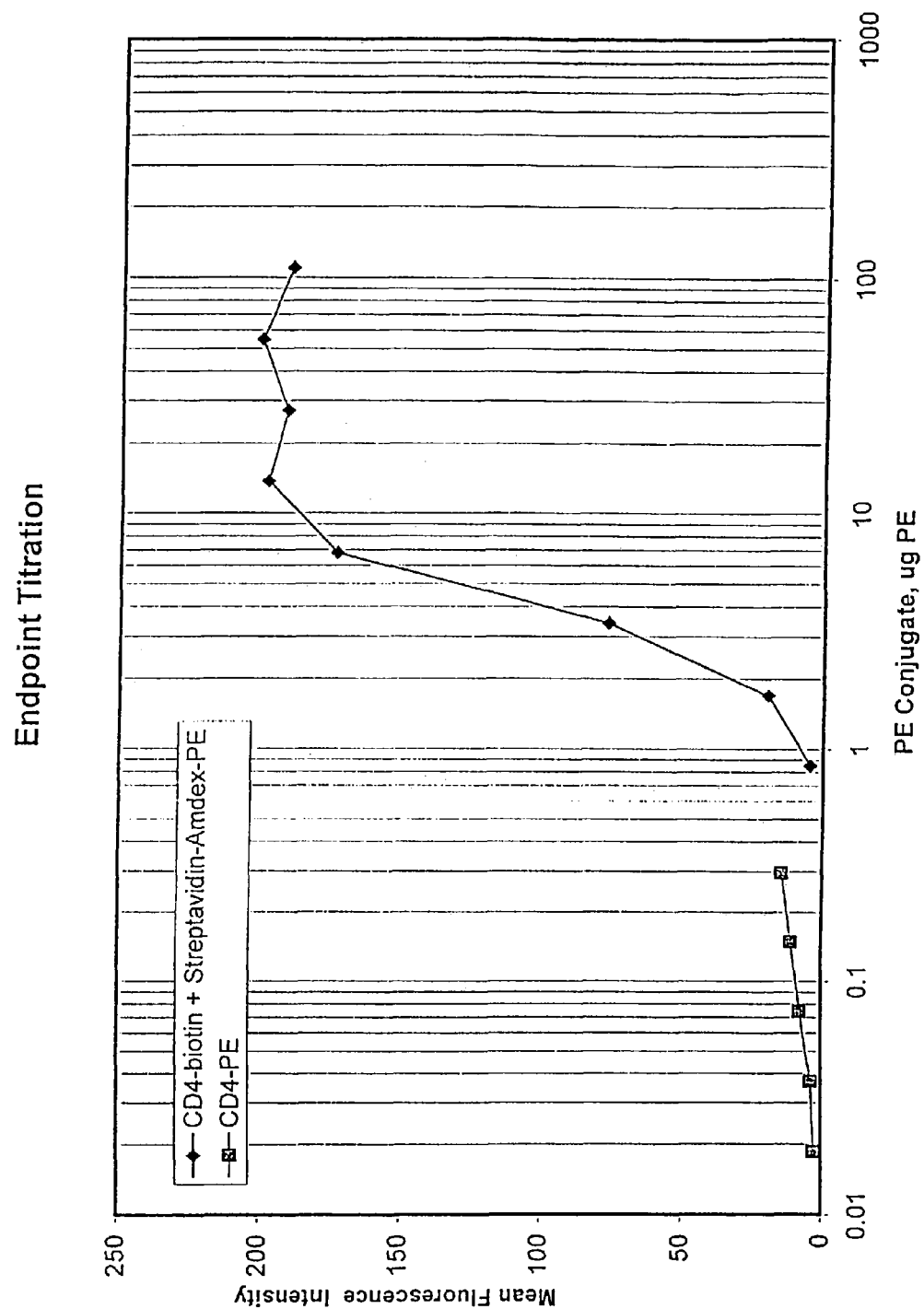
FIG. 9 is a graph showing endpoint titration, plotting mean fluorescence intensity vs. PE conjugate, measured in micrograms of PE. The CD4-biotin and streptavidin-Amdex-PE (♦) made with the improved Amdex of the invention was compared with the control CD4-PE (■). These data indicate the superiority of the improved reagent over the standard bottled product with regard to fluorescence intensity and how that intensity is directly related to the amount of PE included in the conjugate.

FIG. 9 and Table 9 reveal flow cytometric data for an endpoint titration run with ImmunoTrol™ cells (Beckman Coulter, Inc.). The table lists the reagents used, the mass of reagent, StreptAvidin-Amdex-PE, or the control CD4-PE. Titers are reported in micrograms per test and Mean Fluorescence Intensity (MFI) is recorded. Note that anti-CD4-PE, Cat. No. IM0449, lot 47, had an antibody concentration of 2.5 μg/mL, and an F/P ratio of 0.99. Also, the streptavidin and PE concentrations in the pooled fractions of amplification reagent before addition of ECD stabilization buffer were 0.104 mg/mL and 0.633 mg/mL, respectively.

TABLE 9

| Reagent | Streptavidin/test (μg) | Phycoerythrin (PE)/test (μg) | MFI |
|---|---|---|---|
| CD4-biotin + StrAv-Amdex-PE | 18 | 110 | 190.1 |
| CD4-biotin + StrAv-Amdex-PE | 9.0 | 55 | 200.7 |
| CD4-biotin + StrAv-Amdex-PE | 4.5 | 27 | 191.4 |
| CD4-biotin + StrAv-Amdex-PE | 2.2 | 14 | 198.1 |
| CD4-biotin + StrAv-Amdex-PE | 1.1 | 6.8 | 173.2 |
| CD4-biotin + StrAv-Amdex-PE | 0.56 | 3.4 | 76.6 |
| CD4-biotin + StrAv-Amdex-PE | 0.28 | 1.7 | 19.7 |
| CD4-biotin + StrAv-Amdex-PE | 0.14 | 0.85 | 4.39 |

| | CD4/test (μg) | PE/test (μg) | MFI |
|---|---|---|---|
| CD4-PE, bp | 0.20 | 0.30 | 14.2 |
| CD4-PE, bp | 0.10 | 0.15 | 10.7 |
| CD4-PE, bp | 0.050 | 0.074 | 7.47 |
| CD4-PE, bp | 0.025 | 0.037 | 3.52 |
| CD4-PE, bp | 0.012 | 0.019 | 2.43 |

The PE mass (μgs) at first approach of the plateau (or first saturation of antigenic sites on cells) in the titration curve of FIG. 9 is about 0.3 for the direct CD4-PE conjugate versus about 14 for Streptavidin-Amdex-PE conjugate. Thus, 46.7 times more PE was used to obtain saturation in the latter titer curve. At the same time, the PE fluorescence amplification factor is 198.1/14.2=13.95. This factor lags behind the mass ratio by a factor of 3.3. About one-third less of the biotinylated-CD4+StrAv-Amdex-PE conjugate added to the same amount of cellular sample at the used titers is binding to the targeted antigenic sites of cells compared to the amount of CD4-PE conjugate that is binding to the same cells. Previous analysis of CD4-PE binding data (see Table II in U.S. Pat. No. 5,814,468) showed variable fractions of bound conjugate between 0.11 and 0.36 at similar points on the binding curve. Thus, some of the conjugate is in solution.

All documents cited above are incorporated by reference herein. The compositions and processes of the present invention are believed to be encompassed by the scope of the claims appended hereto.

The invention claimed is:

1. A composition comprising polydisperse aminodextran polymer molecules, said composition being soluble in an aqueous solution at a concentration of 10 mg/ml, said molecules having a narrow size distribution characterized by an average molecule mean hydrodynamic diameter of greater than 115 nm, a polydispersity index of between 0.10 and 0.47, an average molecular weight (MW) greater than 3 million daltons, and an amine content of greater than 50 amines per molecule.

2. The composition according to claim 1, wherein said average MW is greater than 4 MDa.

3. The composition according to claim 1, wherein said average MW is greater than 5 MDa.

4. The composition according to claim 1, wherein said average MW is greater than 6 MDa.

5. The composition according to claim 1, wherein said average MW is greater than 7 MDa.

6. The composition according to claim 1, wherein said average MW is greater than 8 MDa.

7. The composition according to claim 1, wherein said amine content is between 50 to 130 amines per molecule.

8. The composition according to claim 1, which is soluble in an aqueous solution at a concentration of between 10 to 50 mg/ml.

9. The composition according to claim 1, wherein said average molecule mean hydrodynamic diameter is greater than 125 nm.

10. The composition according to claim 1, wherein said average molecule mean hydrodynamic diameter is greater than 150 nm.

11. The composition according to claim 10, wherein said fractionation is performed using column chromatography.

12. The composition according to claim 1, prepared by separating from a first mixture of polydisperse aminodextran particles of a wide size distribution characterized by an average molecule mean hydrodynamic diameter of less than 115 nm, and a polydispersity index greater than 0.40, a second mixture of polydisperse aminodextran polymer molecules having a narrow size distribution characterized by an average molecule mean hydrodynamic diameter of greater than 115 nm, a polydispersity index of between 0.10 and 0.47, an average molecular weight (MW) greater than 3 million daltons, and an amine content of greater than 50 amines per molecule, wherein said second mixture of separated molecules is soluble in an aqueous solution at a concentration of 10 mg/mL.

13. The composition according to claim 12, wherein said separating is performed by fractionation.

14. A composition comprising a conjugate comprising the soluble polydisperse aminodextran molecules of claim 1, conjugated to a selected labeled protein.

15. The composition according to claim 14, wherein said labeled protein is a fluorescent protein or a protein labeled with a fluorescent protein.

16. The composition according to claim 15, wherein said fluorescent-labeled protein is an antibody labeled with a fluorescent molecule or dye.

17. A cell labeling reagent comprising a composition comprising polydisperse aminodextran polymer molecules, said composition being soluble in an aqueous solution at a concentration of 10 mg/mL, said molecules having a narrow size distribution characterized by an average molecule mean hydrodynamic diameter of greater than 115 nm, a polydispersity index of between 0.10 and 0.47, an average molecular weight (MW) greater than 3 million daltons, and an amine content of greater than 50 amines per molecule, wherein said molecules are conjugated via said amines to selected labeled proteins.

18. The reagent according to claim 17, wherein said labeled protein is an antibody labeled with a fluorescent molecule or dye.

19. A method for producing cell labeling reagents comprising the steps of:
  (a) providing a composition containing polydisperse aminodextran polymer molecules, said composition being soluble in an aqueous solution at a concentration of 10 mg/mL, said molecules having a narrow size distribution characterized by an average molecule mean hydrodynamic diameter of greater than 115 nm, a polydispersity index of between 0.10 and 0.47, an average molecular weight (MW) greater than 3 million daltons, and an amine content of greater than 50 amines per molecule; and
  (b) conjugating said molecules via said amines to selected labeled proteins.

20. The method according to claim 19, further wherein said composition is prepared by the steps of:
  i. separating from a first mixture of polydisperse aminodextran particles of a wide size distribution characterized by an average molecule mean hydrodynamic diameter of less than 115 nm, and a polydispersity index greater than 0.4, a second mixture of polydisperse aminodextran polymer molecules having a narrow size distribution characterized by an average molecule mean hydrodynamic diameter of greater than 115 nm, a polydispersity index of between 0.10 and 0.47, an average molecular weight (MW) greater than 3 million daltons, and an amine content of greater than 50 amines per molecule, wherein said second mixture of separated molecules is soluble in an aqueous solution at a concentration of 10 mg/ml;
  ii. lyophilizing said second mixture (i); and
  iii. redissolving said lyophilized second mixture in an aqueous solution.

* * * * *